(12) United States Patent
Jagtap et al.

(10) Patent No.: US 7,381,722 B2
(45) Date of Patent: Jun. 3, 2008

(54) TETRACYCLIC AMINO AND CARBOXAMIDO COMPOUNDS AND METHODS OF USE THEREOF

(75) Inventors: Prakash Jagtap, North Andover, MA (US); Csaba Szabo, Budapest (HU)

(73) Assignee: Inotek Pharmaceuticals Corporation, Beverly, MA (US)

(*) Notice: Subject to any disclaimer, the term of this patent is extended or adjusted under 35 U.S.C. 154(b) by 0 days.

(21) Appl. No.: 11/354,707

(22) Filed: Feb. 15, 2006

(65) Prior Publication Data

US 2006/0287312 A1 Dec. 21, 2006

Related U.S. Application Data

(60) Provisional application No. 60/656,636, filed on Feb. 25, 2005.

(51) Int. Cl.
*A61K 31/5377* (2006.01)
*C07D 413/12* (2006.01)

(52) U.S. Cl. .................. 514/232.8; 544/125; 546/61; 514/284

(58) Field of Classification Search ............ 514/284, 514/232.8; 546/61; 544/125
See application file for complete search history.

(56) References Cited

U.S. PATENT DOCUMENTS

| | | |
|---|---|---|
| 3,710,795 A | 1/1973 | Higuchi et al. |
| 4,113,731 A | 9/1978 | Winters et al. |
| 4,263,304 A | 4/1981 | Ishizumi et al. |
| 5,079,246 A | 1/1992 | Forbes et al. |
| 5,177,075 A | 1/1993 | Suto et al. |
| 5,260,316 A | 11/1993 | Van Duzer et al. |
| 5,262,564 A | 11/1993 | Kun et al. |
| 5,597,831 A | 1/1997 | Michalsky et al. |
| 5,710,162 A | 1/1998 | Okazaki et al. |
| 5,733,918 A | 3/1998 | Okazaki et al. |
| 6,028,079 A | 2/2000 | Okazaki et al. |
| 6,277,990 B1 | 8/2001 | Jagtap et al. |
| 6,346,535 B1 | 2/2002 | Cotter et al. |
| 6,346,536 B1 | 2/2002 | Li et al. |
| 6,498,194 B2 | 12/2002 | Cotter et al. |
| 6,635,642 B1 | 10/2003 | Jackson et al. |
| 6,828,319 B2 | 12/2004 | Jagtap et al. |
| 6,956,035 B2 | 10/2005 | Jagtap et al. |
| 7,217,709 B2 | 5/2007 | Jagtap et al. |
| 2002/0099063 A1 | 7/2002 | Cotter et al. |
| 2003/0039628 A1 | 2/2003 | Hellstrand et al. |
| 2004/0039009 A1 | 2/2004 | Jagtap et al. |
| 2004/0077667 A1 | 4/2004 | Matsuoka et al. |
| 2004/0120926 A1 | 6/2004 | Hellstrand et al. |
| 2004/0229895 A1 | 11/2004 | Jagtap et al. |
| 2005/0228007 A1 | 10/2005 | Japtap et al. |
| 2005/0261288 A1 | 11/2005 | Jagtap et al. |
| 2006/0019980 A1 | 1/2006 | Szabo et al. |
| 2006/0079510 A1 | 4/2006 | Hellstrand et al. |
| 2006/0287311 A1 | 12/2006 | Jagtap et al. |
| 2006/0287313 A1 | 12/2006 | Jagtap et al. |
| 2007/0049555 A1 | 3/2007 | Jagtap et al. |

FOREIGN PATENT DOCUMENTS

| | | |
|---|---|---|
| CA | 2349227 | 5/2000 |
| GB | 2025932 A | 1/1980 |
| JP | 2003267888 | 9/2003 |
| WO | WO-91/04037 | 4/1991 |
| WO | WO 93/05023 | 3/1993 |
| WO | WO 99/08680 | 2/1999 |
| WO | WO 99/11311 | 3/1999 |
| WO | WO 99/11623 | 3/1999 |
| WO | WO 99/11628 | 3/1999 |
| WO | WO 99/11644 | 3/1999 |
| WO | WO 99/11645 | 3/1999 |
| WO | WO 99/11649 | 3/1999 |
| WO | WO 99/59973 | 11/1999 |
| WO | WO 99/59975 | 11/1999 |
| WO | WO 00/21537 | 4/2000 |
| WO | WO 00/39070 | 7/2000 |
| WO | WO 00/39104 | 7/2000 |
| WO | WO 00/42040 | 7/2000 |
| WO | WO 01/12199 | 2/2001 |
| WO | WO 02/06284 | 1/2002 |
| WO | WO 2004/014862 | 2/2004 |
| WO | WO 2004/043959 | 5/2004 |
| WO | WO 2005/012524 | 2/2005 |
| WO | WO 2005/053662 | 6/2005 |
| WO | WO 2005/082079 | 9/2005 |
| WO | WO 2005/082368 | 9/2005 |
| WO | WO 2006/009718 A2 | 1/2006 |
| WO | WO-2006/039545 A3 | 4/2006 |

OTHER PUBLICATIONS

Abdelkarim et al., Protective effects of PJ34, a novel, potent inibitor of poly(ADP-ribose) polymerase (PARP) in in vitro and in vivo models of stroke, Int. J. Mol. Med., 7:255-260, 2001.
Aldrich, p. 32, Aldrich Chemical Company, 1992.
Ando et al., Cyclization reactions of 1,2-bis(2-cyanophenyl_propionitriles. II. Synthesis of 5-amino-4,7-dimethoxy-11H-indo[1,2-c]isoquinolin-11-one, Bull. Chem. Soc. Japan, 47:1014-17, 1974.
Banasik et al., Specific inhibitors of poly(ADP-ribose) synthetase and mono(ADP-ribosyl)transferase, J. Biol. Chem., 267:1569-75, 1992.

(Continued)

*Primary Examiner*—Charanjit S. Aulakh
(74) *Attorney, Agent, or Firm*—Wilmer Cutler Pickering Hale and Dorr LLP

(57) ABSTRACT

The present invention relates to Tetracyclic Amino Compounds and Tetracyclic Carboxamido Compounds, compositions comprising an effective amount of a Tetracyclic Amino Compound or a Tetracyclic Carboxamido Compound and methods for treating or preventing an inflammatory disease, a reperfusion injury, diabetes, a diabetic complication, reoxygenation injury resulting from organ transplantation, an ischemic condition, Parkinson's disease, renal failure, a vascular disease, a cardiovascular disease, or cancer, comprising administering to a subject in need thereof an effective amount of a Tetracyclic Amino Compound or a Tetracyclic Carboxamido Compound.

29 Claims, No Drawings

OTHER PUBLICATIONS

Banasik et al., Inhibitors and activators of ADP-ribosylation reactions, Mol. Cell. Biochem., 138:185-97, 1994.

Bloch et al., The role of the 5'-hydroxyl group of adenosine in determining substrate specificity for adenosine deaminase, J. Med. Chem., 10(5):908-912, 1967.

Burger's Medicinal Chemistry and Drug Discovery, 5th ed., vol. 1: Principles and Practice, John Wiley and Sons, Inc., pp. 975-977, 1994.

Chatterjea et al., Cyclisation of alpha-benzylhomophthalic acids, Experientia, 16:439-440, 1960.

Chatterjea et al., On 4-Keto-3:4-Dihydroisocoumarin, J. Indian Chem. Soc. 44(11):911-919, 1967.

Cushman et al., Synthesis of new indeno[1,2b]isoquinolines: Cytotoxic non-camptothecin topoisomerase I inhibitors, J. Med. Chem., 43(20):3688-3698, 2000.

Dusemund et al., 5-hydroxyisoindolo[2,1b]isoquinolin-7-one: Synthesis and isomerization, Arch. Pharm (Weinheim, Ger.), 317:381-2, 1984.

Griffin et al., Resistance-modifying agents. 5. Synthesis and biological properties of quinazolinone inhibitors of the DNA repair enzyme poly(ADP-ribose) polymerase (PARP), J. Med. Chem., 41:5247-5256, 1998.

Grupp et al., Protection against hypoxia-reoxygenation in the absence of poly9ADP-ribose) synthetase in isolated working hearts, J. Mol. Cell Cardiol., 31:297-303, 1999.

Hakimelahi et al., Ring Open Analogues of Adenine Nucleoside, Aminoacyl Derivatives of Cyclo- and Acyclo-nucleosides, Helvetica Chemica Acta, 70:219-231, 1987.

Herzog et al., Annu Rev Gerentol Geriatr 9:74-119 (1989).

Hiremath et al., A New Method for the Synthesis of 6H,11H-Indolo[3,2-c]-isoquinolin-5-ones/thiones and their Reactions, J. Heterocyc. Chem., 30(3):603-609, 1993.

Hiremath et al., Synthesis of Substituted 7H-Indolo[2,3-c] isoquinolines, Indian Journal of Chemistry, Section B 24B(12):1235-1238, 1985.

Hiremath et al., Synthesis and Biological Evaluation of Some Substituted 5H, 6H, 7H,-Indolo[2,3-C] Isoquinolin-5-thiones and their Derivatives, Indian Journal of Heterocyclic Chemistry 3(1):37-42, 1993.

Hiremath et al., Synthesis of [10-substituted-6H,7H-indolo[2,3-c]iso-quinolin-5-one-6-yl]acetyl-3,5-disubstituted-pyrazoles/pryazolones and 5-[10-substituted-6H,7H-indolo[2,3-c]iso-quinolin-5-one-6-yl]methyl-1,3,4-oxadiazol-2-thiones, Journal of the Indian Chemical Society 72(10):735-738, 1995.

Hiremath et al., Synthesis and Biological Studies of Some New Brideghead Nitrogen Heterocycles Containing Indoloisoquinoline Nucleus, Oriental Journal of Chemistry 13(2):173-176, 1997.

Hiremath et al., Synthesis of substituted 2-(5-oxo/thioxo-1,3,4-oxadiazol-2-yl)-indoles & 2-(5-oxo/thioxo-1,3,4-oxadiazol-2-ylamino)indoles, Indian Journal of Chemistry, Section B 22B(6):571-576, 1983.

Jagtap et al., Discovery of Potent Poly(ADP-ribose) Polymerase-1 Inhibitors from the Modification of Indeno[1,2-c]isoquinolinone, J. Med. Chem. 2005, 48, 5100-5103.

Jantzen and Robinson, Modern Pharmaceutics, 3rd ed., eds. Baker and Rhodes, p. 596, 1995.

Jha et al., Synthesis of Indeno[2,1-c] isocoumarins and indeno[2,1-c]isoquinolones, Indian Journal of Chemistry, Section B 24B(4):440-444, 1985.

Kawana et al., Nucleoside Peptides. III. The Synthesis of N-[1-(9-Adenyl)-β-D-ribofuranuronosyl] Derivatives of Certain Amino Acids and Peptides, J. Org. Chem., 37(2):288-290, 1972.

Kirby et al., Hydride hyperconjugation in 1(3)-methylazulenes, Tetrahedron Lett., 27:1-4, 1960.

Kirby et al., 4,6,8-trimethylazulenium percholrate, Chemistry & Industry (London, UK), 1217-1218, 1960.

Lal et al., Applications of carbon-nitrogen bond cleavage reaction: A synthesis/derivisation of 11H-indeno[1,2-c]isoquinolones, Indian J. Chem., Sect. B, 38B:33-39, 1999.

Lamping et al., LPS_binding protein protects mice from septic shock caused by LPS or gram-negative bacteria, J. Clin. Invest., 101(10):2065-2071, 1998.

Mabley et al., Inhibition of poly(ADP-ribose) synthetase by gene disruption or inhibitin with 5-iodo-6-amino-1,2-benzopyrone protects mice from multiple-low-dose-streptozotocin-induced diabetes, Br. J. Pharmacol., 133(6):909-919, 2001.

Mandir et al., A novel in vivo post-translational modification of p53 by PARP-1 in MPTP-induced parkinsonism, J. Neurochem., 83(1):186-192, 2002.

Mandir et al., Poly(ADP-ribose) polymerase activation mediates 1-methyl-4-phenyl-1, 2,3,6-tetrahydropyridine (MPTP)-induced parkinsonism, Proc. Natl. Acad. Sci. U.S.A., 96(10):5774-5779, 1999.

Milam et al., Inhibitors of poly(adenosine diphosphate-ribose) synthesis: effect on other metabolic processes. Science, 223:589-591, 1984.

Morrison and Boyd, Organic Chemistry, 5th ed., Allyn and Bacon, Inc., p. 179, 1987.

Ohno et al., Modulation of adenosine receptor affinity and intrinsic efficacy in adenine nucleosides substituted at the 2 position, Biorg. Med. Chem., 12:2995-3007, 2004.

Ojika et al, Ptaquiloside, a Potent Carcinogen Isolated From Bracken Fern *Pteridium aquilinum* Var. *latiusculum*: Structure Elucidation Based On Chemical and Spectral Evidence, and Reactions with Amino Acids, Nucleosides, and Nucleotides, Tetrahedron, 43(22):5261-5274, 1987.

Parrillo, Pathogenic mechanisms of septic shock, N. Eng. J. Med., 328:1471-1477, 1993.

Peukert and Schwhan, Expert Opin. Ther. Patents 14(11):1531-1551 (2004).

Shinkwin et al., Synthesis of thiophenecarboxamides, thieno[3,4-c]pyridin-4(5H)-ones and thieno[3,4-d]pyrimidin-4(3H)-ones and preliminary evaluation as inhibitors of poly(ADP-ribose)polymerase (PARP). Bioorg. Med. Chem., 7:297-308, 1999.

Soriano et al., Diabetic endothelial dysfunction: the role of poly(ADP-ribose) polymerase activation. Nature Medicine, 7(1):108-113, 2001.

Southan Szabo, Poly(ADP-ribose) polymerase inhibitors, Curr. Med. Chem., 10:321, 2003.

Srivastava et al., Synthesis of Indeno[2,1-c] isocoumarins and indeno[2,1-c]isoquinolones, Journal of the Indian Chemical Society 66(4):276-81, 1989.

Strumberg et al., Synthesis of cytotoxic indenosoquinoline topoisomerase I poisons, J. Med. Chem., 42(3):446-457, 1999.

Szabo et al., The pathophysiological role of peroxynitrite in shock, inflammation, and ischemia-reperfusion injury. Shock 6:79-88, 1996.

Szabo et al., Role of poly(ADP-ribose) synthetase in inflammation and ischaemia-reperfusion. Trends Pharmacol. Sci. 19:287-98, 1998.

Virag et al., Peroxynitrite-induced thymocyte apoptosis: the role of caspases and poly(ADP-ribose) synthetase (PARP) activation, Immunol., 94(3):345-355, 1998.

Wang et al., Apoptosis inducing factor and PARP-mediated injury in the MPTP mouse model of Parkinson's disease, Ann N.Y. Acad. Sci., 991:132-139, 2003.

Wawzonek et al., The Synthesis and Reactions of 1-Carbamyl-11-ketoindeno[1,2-c]isoquinoline, J. Org. Chem. 1966, 31:1004-1006.

Wawzonek et al., Synthesis of 6-substituted-6H-indeno[1,2-c]isoquinoline-5,11-diones, Org. Prep. Proc. Int., 14:163-8, 1982.

Wawzonek et al., Preparation and reactions of 4b-acetoxy-4b,9b-dihydroindeno[2,1-a]indene-5,10-dione, Can. J. Chem., 59:2833, 1981.

White et al., Resistance-modifying agents. 9. Synthesis and biological properties of benzimidazole inhibitors of the DNA repair enzyme poly(ADP-ribose) polymerase, J. Med. Chem., 43:4084-4097, 2000.

Winters et al., Synthesis and biological activities of some indolo[2,3-c]isoquinoline derivatives. Farmaco. Ed. Sci. 34(6):507-517, 1979.

Yamaguchi et al., The Synthesis of Benzofuroquinolines. IX. A Benzofuroisoquinolinone and a Benzofuroisocoumarin, J. Hetercycl. Chem., 32(2):419-423, 1995.

Yamaguchi et al., The synthesis of benzofuroquinolines. X. Some benzofuro[3,2-c]isoquinoline derivatives, J. Hetercycl. Chem., 32(5):1517-1519, 1995.

Zhang et al., GPI 6150 prevents H(2)O(2) cytotoxicity by inhibiting poly(ADP-ribose) polymerase. Biochem. Biophys. Res. Commun., 278:590-98, 2000.

Jagtap, Prakash G., Baloglu, Erkan, Southan, Garry, Williams, William, Roy, Aloka, Nivorozhkin, Alexander, Landrau, Nelson, Desisto, Kevin, Salzman, Andrew L. and Szabó, Csaba (2005) Facile and Convenient Syntheses of 6,11-Dihydro-5$H$-indeno[1,2-$c$]isoquinolin-5-ones and 6,11-Dihydro-5$H$-indolo[3,2-$c$]isoquinolin-5-one. Organic Letters, vol. 7, No. 9, 1753-1756.

Jagtap, Prakash and Szabó, Csaba (2005) Poly(ADP-Ribose) Polymerase and the Therapeutic Effects of Its Inhibitors. Nature Reviews, Drug Discovery, vol. 4, 421-440.

Andrasi, T. et al., 2005, "Poly(ADP-ribose) polymerase inhibitor PJ-34 reduces mesenteric vascular injury induced by experimental cardiopulmonary bypass with cardiac arrest," Am J Physiol Heart Circ Physiol, vol. 288:H2972-H2978.

Beller, C. et al., 2006, "Poly(ADP-ribose) Polymerase Inhibition Combined with Irradiation: A Dual Treatment Concept to Prevent Neointimal Hyperplasia After Endarterectomy," Int, J. Radiation Oncology Biol. Phys., vol. 66(3) 867-875.

Besson, V. et al., 2005, "Beneficial effect of PJ34 and INO-1001, two novel water-soluble poly(ADP-ribose) polymerase inhibitors, on the consequences of traumatic brain injury in rat," Brain Research, vol. 1041: 149-156.

Black, J. et al., 2006, "Poly Adenosine Diphosphate-Ribose Polymerase Inhibitor PJ34 Abolishes Systemic Proinflammatory Responses to Thoracic Aortic Ischemia and Reperfusion," J Am Coll Surg., vol. 203:44-53.

Boulares, A., et al. 2003, "Gene Knockout of Pharmacological Inhibition of Poly(ADP-Ribose) Polymerase-1 Prevents Lung Inflammation in a Murine Model of Asthma," Am J. Respir. Cell Mol. Biol., vol. 28: 322-329.

Burkart, V. et al., 1999, "Mice lacking the poly(ADP-ribose) polymerase gene are resistant to pancreatic beta-cell destruction and diabetes development induced by streptozocin," Nature Medicine, vol. 5(3): 314-319.

Calabrese, C. et al., 2004, "Anticancer Chemosensitization and Radiosensitization by the Novel Poly(ADP-ribose) Polymerase-1 Inhibitor AG14361," J Natl Cancer Inst., vol. 96: 56-67.

Chiang, S. et al., 2000, "Post-Treatment at 12 or 18 Hours with 3-Aminobenzamide Ameliorates Retinal Ischemia-Reperfusion Damage," Invest Ophthalmol Vis Sci., vol. 41: 3210-3214.

Conde, C. et al., 2001, "Loss of poly (ADP-ribose) polymerase-1 causes increased tumour latency in p53-deficient mice," The EMBO Journal, vol. 20(13): 3535-3543.

Cosi, C. et al., 2002, "New inhibitors of poly(ADP-ribose) polymerase and their potential therapeutic targets," Expert Opin. Ther. Patents, vol. 12(7): 1047-1071.

Cuzzocrea, S. et al., 1997, "Beneficial effects of 3-aminobenzamide, an inhibitor of poly (ADP-ribose) synthetase in a rat model of splanchnic artery occlusion and reperfusion," British Journal of Pharmacology, vol. 121:1065-1074.

Demiryurek, A. et al., 2002, "Protective Effects of Poly (ADP-Ribose) Synthase Inhibitors on Digoxin-Induced Cardiotoxicity in Guinea-Pig Isolated Hearts," Pharmacological Research, vol. 45(3):189-194.

Eliasson, M. et al., 1997, "Poly(ADP-ribose) polymerase gene disruption renders mice resistant to cerebral ischemia," Nature Medicine, vol. 3(10): 1089-1095.

Farivar, A. et al., 2005, "Poly (ADP) Ribose Polymerase Inhibition Improves Rat Cardiac Allograft Survival," Ann Thorac Surg., vol. 80: 950-956.

Farkas, B. et al., 2001, "Reduction of acute photodamage in skin by topical application of a novel PARP inhibitor," Biochemical Pharmacology, vol. 63: 921-932.

Farmer, H. et al., 2005, "Targeting the DNA repair defect in BRCA mutant cells as a therapeutic strategy," Nature, vol. 434: 917-921.

Halmosi, R. et al., 2001, "Effect of Poly(ADP-Ribose) Polymerase Inhibitors on the Ischemia-Reperfusion-Induced Oxidative Cell Damage and Mitochondrial Metabolism in Langendorff Heart Perfusion System," Mol Pharmacol, vol. 59: 1497-1505.

Holl, V. et al., 2000, "Modulation of the Antiproliferative Activity of Anticancer Drugs in Hematopoietic Tumor Cell Lines by the Poly(ADP-Ribose) Polymerase Inhibitor 6(5-H)-Phenanthridinone," Anticancer Research, vol. 20: 3233-3242.

Horsman, M. et al., 1987, "Radiosensitization by Nicotinamide in Vivo: A Greater Enhancement of Tumor Damage Compared to That of Normal Tissues," Radiation Research, vol. 109: 479-489.

Horsman, M. et al., 1997, "Nicotinamide as a radiosensitizer in tumours and normal tissues: the importance of drug dose and timing," Radiotherapy and Oncology, vol. 45: 167-174.

Hua, H. et al., 2005, "Polyadenosine Diphosphate-Ribose Polymerase Inhibition Modulates Skeletal Muscle Injury Following Ischemia Reperfusion," Arch Surg., vol. 140:344-351.

Iwashita, A. et al., 2004, "Neuroprotective Effects of a Novel Poly(ADP-Ribose) Polymerase-1 Inhibitor, 2-(3-[4-(4-Chlorophenyl)-1-piperazinyl] propyl)-4(3H)-quinazolinone (FR255595), in an in Vitro Model of Cell Death and in Mouse 1-Methyl-4-phenyl-1,2,3,6-tetrahydropyridine Model of Parkinson's Disease," The Journal of Pharmacology and Experimental Therapeutics, vol. 309(3): 1067-1078.

Jagtap, P. et al., 2002, "Novel phenanthridinone inhibitors of poly(adenosine 5'-diphosphate-ribose) synthetase: Potent cytoprotective and antishock agents," Crit Care Med., vol. 30: 1071-1082.

Jijon, H. et al., 2000, "Inhibition of poly(ADP-ribose) polymerase attenuates inflammation in a model of chronic colitis," Am J Physiol Gastrointest Liver Physiol, vol. 279: G641-G651.

Kelland, L. et al., 1989, "The effect of 3-aminobenzamide in the radiation response of three human cervix carcinoma xenografts," Radiotherapy and Oncology, vol. 15: 363-369.

Khandoga, A. et al., 2004, "5-Aminoisoquinolinone, a novel inhibitor of poly(adenosine disphosphate-ribose) polymerase, reduces microvascular liver injury but not mortality rate after hepatic ischemia-reperfusion," Crit Care Med., vol. 32: 472-477.

Koch, S. et al., 2002, "Novel Tricyclic Poly(ADP-ribose) Polymerase-1 inhibitors with Potent Anticancer Chemopotentiating Activity: Design, Synthesis, and X-ray Cocrystal Structure," J. Med. Chem., vol. 45: 4961-4974.

Koedel, U. et al., 2002, "Meningitis-Associated Central Nervous System Complications Are Mediated by the Activation of Poly(ADP-ribose) Polymerase," Journal of Cerebral Blood Flow & Metabolism, vol. 22: 39-49.

Li, F. et al., 2004, "Evaluation of orally active poly(ADP-ribose) polymerase inhibitor in streptozotocin-diabetic rat model of early peripheral neuropathy," Diabetologia, vol. 47:710-717.

Liaudet, L. et al., 2002, "Activation of Poly(ADP-Ribose) Polymerase-1 Is a Central Mechanism of Lipopolysaccharide-Induced Acute Lung Inflammation," Am J Respir Crit Care Med., vol. 165: 372-377.

Liaudet, L. et al., 2000, "Poly (ADP-Ribose) Synthetase Mediates Intestinal Mucosal Barrier Dysfunction After Mesenteric Ischemia," Shock, vol. 14(2): 134-141.

Liaudet, L. et al., 2000, "Protection against hemorrhagic shock in mice genetically deficient in poly(ADP-ribose) polymerase." PNAS, vol. 97(18): 10203-10208.

Liaudet, L. et al., 2001, "Suppression of poly (ADP-ribose) polymerase activiation by 3-aminobenzamide in a rat model of myocardial infarction: long-term morphological and functional consequences," British Journal of Pharmacology, vol. 133: 1424-1430.

Lohinai, Z. et al., 2003, "Role of the Activation of the Nuclear Enzyme Poly(ADP-Ribose) Polymerase in the Pathogensis of Periodontitis," J Dent Res., vol. 82(12): 987-992.

Mabley, J. et al., 2001, "Anti-inflammatory effects of a novel, potent inhibitor of poly (ADP-ribose) polymerase," Inflamm. Res., vol. 50: 561-569.

Martin, D. et al., 2000, "Inhibition of poly (ADP-ribose) polymerase attenuates ischemic renal injury in rats," Am J Physiol Regulatory Integrative Comp Physiol, vol. 279: R1834-R1840.

Martin-Oliva, D. et al., 2004, "Crosstalk between PARP-1 and NF-КB modulates the promotion of skin neoplasia," Oncogene, vol. 23: 5275-5283.

Martin-Oliva, D. et al., 2006, "Inhibition of Poly(ADP-Ribose) Polymerase Modulates Tumor-Related Gene Expression, Including Hypoxia-Inducible Factor-1 Activation, During Skin Carcinogenesis," Cancer Res, vol. 66(11): 5744-5756.

Mazzon, E. et al., 2002, "GPI 6150, a PARP inhibitor, reduces the colon injury caused by dinitrobenzene sulfonic acid in the rat," Biochemical Pharmacology, vol. 64: 327-337.

McDonald, M. et al., 1999, "Effects of inhibitors of the activity of poly (ADP-ribose) synthetase on the organ injury and dysfunction caused by haemorrhagic shock," British Journal of Pharmacology, vol. 128: 1339-1345.

McDonald, M. et al., 2000, "Effects of 5-aminoisoquinolinone, a water-soluble, potent inhibitor of the activity of poly (ADP-ribose) polymerase on the organ injury and dysfunction caused by haemorrhagic shock," British Journal of Pharmacology, 130: 843-850.

Miknyoczki, S. et al., 2003, "Chemopotentiation of Temozolomide, Irinotecan, and Cisplatin Activity by CEP-6800, a Poly(ADP-Ribose) Polymerase Inhibitor," Molecular Cancer Therapeutics, vol. 2: 371-382.

Mota, R. et al., 2005, "Inhibition of poly(ADP-ribose) polymerase attenuates the severity of acute pancreatitis and associated lung injury," Laboratory Investigation, vol. 85: 1250-1262.

Nozaki, T. et al., 2003, "Parp-1 deficiency implicated in colon and liver tumorigenesis induced by azoxymethane," Cancer Sci., vol. 94: 497-500.

Obrosova, I. et al., 2004, "Role of Poly(ADP-Ribose) Polymerase Activation in Diabetic Neuropathy," Diabetes, vol. 53: 711-720.

Ogawa, K. et al., 2006, "Parp-1 deficiency does not enhance liver carcinogenesis induced by 2-amino-3-methylimidazo[4,5-f]quinoline in mice," Cancer Letters, vol. 236: 32-38.

Oliver, F. et al., 1999, "Resistance to endotoxic shock as a consequence of defective NF-K8 activation in poly (ADP-ribose) polymerase-1 deficient mice," The EMBO Journal, vol. 18(16): 4446-4454.

Pacher, P. et al., 2002, "The Role of Poly(ADP-Ribose) Polymerase Activiation in the Development of Myocardial and Endothelial Dysfunction in Diabetes," Diabetes, vol. 51:514-521.

Pacher, P. et al., 2004, "A New, Potent Poly(ADP-ribose) Polymerase Inhibitor Improves Cardiac and Vascular Dysfunction Associated with Advanced Aging," JPET, vol. 311(2): 485-491.

Pacher, P. et al., 2006, "Beneficial effects of a novel ultrapotent poly(ADP-ribose) polymerase inhibitor in murine models of heart failure," International Journal of Molecular Medicine, vol. 17: 369-375.

Petrilli, V. et al., 2004, "Noncleavable poly(ADP-ribose) polymerase-1 regulates the inflammation response in mice," Journal of Clinical Investigation, vol. 114(8): 1072-1081.

Pieper, A. et al., 1999, "Poly (ADP-ribose) polymerase-deficient mice are protected from streptozotocin-induced diabetes," Proc. Natl. Acad. Sci., vol. 96: 3059-3064.

Pieper, A. et al., 2000, "Myocardial Postischemic Injury Is Reduced by PolyADPribose Polymerase-1 Gene Disruption," Molecular Medicine, vol. 6(4) 271-282.

Scott, G. et al., 2004, "The Therapeutic Effects of PJ34 [N-(6-Oxo-5,6-dihydrophenanthridin-2-yl)-N,N-dimethylacetamide.HCl], a Selective Inhibitor of Poly(ADP-Ribose) Polymerase, in Experimental Allergic Encephaolmyelitis Are Associated with Immunomodulation," JPET, vol. 310: 1053-1061.

Soriano, F. et al., 2001, "Rapid Reversal of the Diabetic Endothelial Dysfunction by Pharmacological Inhibition of Poly (ADP-Ribose) Polymerase," Circ. Res., vol. 89:684-691.

Suarez-Pinzon, W. et al., 2003, "Poly (ADP-Ribose) Polymerase Inhibition Prevents Spontaneous and Recurrent Autoimmune Diabetes in NOD Mice by Inducing Apoptosis of Islet-Infiltrating Leukocytes," Diabetes, vol. 52:1683-1688.

Suzuki, Y. et al., 2004, "Inhibition of Poly(ADP-Ribose) Polymerase Prevents Allergen-Induced Asthma-Like Reaction in Sensitized Guinea Pigs," JPET, vol. 311: 1241-1248.

Szabados, E. et al., 2000, "BGP-15, a Nicotinic Amidoxime Derivate Protecting Heart from Ischemia Reperfusion Injury through Modulation of Poly(ADP-ribose) Polymerase," Biochem Pharmacol, vol. 59: 937-945.

Szabo, C. et al., 1998, "Protection against peroxynitrite-induced fibroblast injury and arthritis development by inhibition of poly(ADP-ribose) synthase," Proc. Natl. Acad. Sci., vol. 95: 3867-3872.

Szabo, C. et al., 2004, "Angiotensin II-Mediated Endothelial Dysfunction: Role of Poly(ADP-ribose) Polymerase Activation," Molecular Medicine, vol. 10(1-6): 28-35.

Szabo, C. et al., 2006, "Poly(ADP-Ribose) Polymerase Inhibitors Ameliorate Nephropathy of Type 2 Diabetic Lepr$^{db/db}$ Mice," Diabetes, vol. 55: 3004-3012.

Szabo, G. et al., 2002, "Poly(ADP-Ribose) Polymerase Inhibition Reduces Reperfusion Injury After Heart Transplantation," Circ. Res. vol. 90:100-106.

Szabo, G. et al., 2006, "Contractile dysfunction in experimental cardiac allograft rejection: role of the poly (ADP-ribose) polymerase pathway," Transplant Intl., vol. 19: 506-513.

Tentori, L. et al., 2003, "Systemic Administration of GPI 15427, a Novel Poly(ADP-Ribose) Polymerase-1 Inhibitor, Increases the Antitumor Activity of Temozolomide against Intracranial Melanoma, Glioma, Lymphoma," Clinical Cancer Research, vol. 9: 5370-5379.

Tentori, L. et al., 2005, "Poly(ADP-ribose) glycohydrolase inhibitor as chemosensitiser of malignant melanoma for temozolomide," European Journal of Cancer, vol. 41: 2948-2957.

Thiemermann, C. et al., 1997, "Inhibition of the activity of poly(ADP ribose) sythetase reduces ischemia-reperfusion injury in the heart and skeletal muscle," Proc. Natl. Acad. Sci., vol. 94:679-683.

Thomas, H. et al., 2007, "Preclinical Selection of a Novel Poly (ADP-ribose) Polymerase Inhibitor for Clinical Trial," Mol Cancer Ther, vol. 6(3): 945-956.

Tong, W. et al., 2003, "Null Mutation of DNA Strand Break-Binding Molecule Poly(ADP-ribose) Polymerase Causes Medulloblastomas in p53−/− Mice," American Journal of Pathology, vol. 162(1): 343-352.

Tsujiuchi, T. et al., 1990, "Possible involvement of poly ADP-ribosylation in phenobarbital promotion of rat hepatocarcinogenesis," Carcinogenesis, vol. 11(10): 1783-1787.

Tsujiuchi, T. et al., 1991, "Effects of 3-Aminobenzamide on Induction of Multiorgan Carcinogenesis by N-Nitrosobis(2-hydroxypropyl)amine in Hamsters," Jpn. J. Cancer Res., vol. 82: 793-799.

Tsujiuchi, T. et al., 1991, "Effects of 3-aminobenzamide on the post-initiation phase of N-nitrosobis(2-oxopropyl)amine induced pancreatic carcinogenesis in Syrian hamsters," Cancer Letters, vol. 61: 61-66.

Tsutsumi, M. et al., 2001, "Increased susceptibilty of poly(ADP-ribose) polymerase-1 knockout mice to nitrosamine carcinogenicity," Carcinogenesis, vol. 22(1): 1-3.

Veres, B. et al., 2004, "Regulation of Kinase Cascades and Transcription Factors by a Poly(ADP-Ribose) Polymerase-1 Inhibitor, 4-Hydroxyquinazoline, in Lipopolysaccharide-Induced Inflammation in Mice," JPET, vol. 310: 247-255.

Woolley, S. et al., 2004, "Role of Poly (ADP) Ribose Synthetase in Lung Ischemia-Reperfusion Injury," J Heart Lung Transplant, vol. 23: 1290-1296.

Xiao, C. et al., 2005, "Poly(ADP-Ribose) Polymerase Promotes Cardiac Remodeling, Contractile Failure, and Translocation of Apoptosis-Inducing Factor in Murine Experimental of Aortic Banding and Heart Failure," JPET, vol. 312(3): 891-898.

Zheng, J. et al., 2004, "Poly (ADP-ribose) polymerase-1 gene ablation protects mice from ischemic renal injury," Am J Physiol Renal Physiol, vol. 288: F387-F398.

Zheng, L. et al., 2004, "Poly(ADP-Ribose) Polymerase Is Involved in the Development of Diabetic Retinopathy via Regulation of Nuclear Factor-κ8," Diabetes, vol. 53: 2960-2967.

Calabrese, C. R. et.al., Identification of potent nontoxic poly(ADP-ribose) polymerase-1 inhibitors: chemopotentiation and pharmacological studies. *Clin. Cancer Res.* 9, 2711-2718 (2003).

Chiarugi, A. et al. Novel isoquinolinone-derived inhibitors of poly(ADP-ribose) polymerase-1: pharmacological characterization and neuroprotective effects in an in vitro model of cerebral ischemia. J. Pharmacol. Exp. Ther. 305, 943-949 (2003).

Curtin N. PARP-1: A new target for cancer treatment, Cancer Research UK Scientific Yearbook, 52-54 (Mar. 2002).

Faro, R. et al. Myocardial protection by PJ34, a novel potent poly(ADP-ribose) synthetase inhibitor. Ann. Thorac. Surg. 73, 575-81 (2002).

Feng, Y. & LeBlanc M. H. Drug-induced hypothermia begun 5 minutes after injury with a poly(adenosine 5'-diphosphate-ribose) polymerase inhibitor reduces hypoxic brain injury in rat pups. Crit. Care Med. 30, 2420-4 (2002).

Ferraris, D. et al. Design and synthesis of poly ADP-ribose polymerase-1 inhibitors. Part 4. Biological evaluation of aza-5[H]-phenanthridin-6-ones as potent, aqueous-soluble compounds for the treatment of ischemic injuries. J. Med. Chem. 46, 3138-3151 (2003).

Ferraris, D. et al. Design and synthesis of poly(ADP-ribose) polymerase-1 (PARP-1) inhibitors. Part 4: biological evaluation of imidazobenzodiazepines as potent PARP-1 inhibitors for treatment of ischemic injuries. Bioorg. & Med. Chem. 11, 3695-3707 (2003).

Goldfarb, R.D. et al. Protective effects of a novel, potent inhibitor of poly(adenosine 5'-diphosphate-ribose) synthetase in a porcine model of severe bacterial sepsis. Crit. Care Med. 30, 974-80 (2002).

Hattori, K. et al. Rational approaches to discovery of orally active and brain-penetrable quinazolinone inhibitors of poly(ADP-ribose)polymerase. J. Med. Chem. 47, 4151-4154 (2004).

Iwashita, A. et al. A new poly(ADP-ribose) polymerase inhibitor, 2-(4-chlorophenyl)-5-quinoxalinecarboxamide (FR261529), ameliorates methamphetamine-induced dopaminergic neurotoxicity in mice. J. Pharmacol. Exp. Ther. 310, 1114-24 (2004).

Iwashita, A. et al. A novel and potent PARP-1 inhibitor, 5-chloro-2-[3-(4-phenyl-3, 6-dihydro-1(2H)-pyridinyl)propyl]-4(3H)-quinazolinone (FR247304), attenuates neuronal damage in vitro and in vivo models of cerebral ischemia. J. Pharmacol. Exp. Ther. 310, 425-36 (2004).

Jagtap, P. G. et al. The discovery and synthesis of novel adenosine substituted 2,3-dihydro-1-H-isoindol-1-ones: potent inhibitors of poly(ADP-ribose) polymerase-1 (PARP-1). Bioorg. Med. Chem. Lett. 14, 81-85 (2004).

Kamanaka, Y. et al. Neuroprotective effects of ONO-1924H, an inhibitor of poly(ADP-ribose) polymerase (PARP), on cytotoxicity of PC12 cells and ischemic cerebral damage. Life Sci. 76, 151-162 (2004).

Komjati, K. et al. Poly(ADP-ribose) polymerase inhibition protect neurons and the white matter and regulates the translocation of apoptosis-inducing factor in stroke. Int. J. Mol. Med. 13, 373-82 (2004).

Laplaca, M.C. et al. Pharmacologic inhibition of poly(ADP-ribose) polymerase is neuroprotective following traumatic brain injury in rats. J. Neurotrauma., 18, 18, 369-76 (2001).

Mazzon, E. et al. Beneficial effects of GPI 6150, an inhibitor of poly(ADP-ribose) polymerase in a rat model of splanchnic artery occlusion and reperfusion. Shock, 17, 222-7 (2002).

Mazzon, E. et al. GPI 6150, a poly(ADP-ribose) polymerase inhibitor, exhibits an anti-inflammatory effect in rat models of inflammation. Eur. J. Pharmacol., 415, 85-94 (2001).

Nakajima, H. et al., A newly synthesized poly(ADP-ribose) polymerase inhibitor. 2-methyl-3,5,7,8-tetrahydrothipyrano[4,3-d]pyrimidine-4-one (DR2313): pharmacological profiles, neuroprotective effects, and therapeutic time window in cerebral ischemia in rats. J. Pharmacol. Exp. Ther, in press, (2005).

Pacher, P. et al. Endothelial dysfunction in aging animals: the role of poly(ADP-ribose) polymerase activation. Br. J. Pharmacol. 135, 1347-50 (2002).

Pacher, P. et al., Pharmacologic inhibition of poly(adenosine diphosphate-ribose) polymerase may represent a novel therapeutic approach in chronic heart failure. J. Am. Coll. Cardiol. 40, 1006-16 (2002).

Pellicciari, R. et al. Towards new neuroprotective agents: design and synthesis of 4H-thieno[2,3-c] isoquinoline-5-one derivatives as potent PARP-1 inhibitors. Farmaco 58, 851-858 (2003).

Skalitzky, J.D. et al. Tricyclic benzimidazoles as potent poly(ADP-ribose) polymerase-1 inhibitors. J. Med. Chem. 46, 210-213 (2003).

Steinhagen, H., et al., Substituted uracil derivatives as potent inhibitors of poly(ADP-ribose)polymerase-1 (PARP-1). Bioorg. Med. Chem. Lett. 12, 3187-3190 (2002).

Tikhe, J. G. et al. Design, synthesis, and evaluation of 3,4-dihydro-2H-[1,4]diazepino[6,7,1-hi]indol-1-ones as inhibitors of poly(ADP-ribose) polymerase. J. Med. Chem. 47, 5467-5481 (2004).

Zhang, J: Beneficial effect of GPI6150 treatment in multiple animal models of disease. In: Zhang J, C (ed) PARP as a therapeutic target. CRC Press, Boca Raton, FL. 2002. pp. 239-256.

US 7,381,722 B2

TETRACYCLIC AMINO AND CARBOXAMIDO COMPOUNDS AND METHODS OF USE THEREOF

This application claims the benefit of U.S. Provisional application Ser. No. 60/656,636, filed Feb. 25, 2005, which is currently pending, the entirety of which is incorporated herein by reference.

1. FIELD OF THE INVENTION

The present invention relates to Tetracyclic Amino Compounds and Tetracyclic Carboxamido Compounds, compositions comprising an effective amount of a Tetracyclic Amino Compound or a Tetracyclic Carboxamido Compound and methods for treating or preventing an inflammatory disease, a reperfusion injury, diabetes, a diabetic complication, reoxygenation injury resulting from organ transplantation, an ischemic condition, Parkinson's disease, renal failure, a vascular disease, a cardiovascular disease, or cancer, comprising administering to a subject in need thereof an effective amount of a Tetracyclic Amino Compound or a Tetracyclic Carboxamido Compound.

2. BACKGROUND OF THE INVENTION

Inflammatory diseases, such as arthritis, colitis, and autoimmune diabetes, typically manifest themselves as disorders distinct from those associated with reperfusion injuries, e.g., stroke and heart attack, and can clinically manifest themselves as different entities. However, there can be common underlying mechanisms between these two types of disorders. In particular, inflammatory disease and reperfusion injury can induce proinflammatory cytokine and chemokine synthesis which can, in turn, result in production of cytotoxic free radicals such as nitric oxide and superoxide. NO and superoxide can react to form peroxynitrite (ONOO⁻) (Szabó et al., Shock 6:79-88, 1996).

The ONOO⁻-induced cell necrosis observed in inflammatory disease and in reperfusion injury involves the activation of the nuclear enzyme poly (ADP-ribose) synthetase (PARS). Activation of PARS is thought to be an important step in the cell-mediated death observed in inflammation and reperfusion injury (Szabó et al., Trends Pharmacol. Sci. 19:287-98, 1998).

A number of PARS inhibitors have been described in the art. See, e.g., Banasik et al., J. Biol. Chem., 267:1569-75, 1992, and Banasik et al., Mol. Cell. Biochem., 138:185-97, 1994; WO 00/39104; WO 00/39070; WO 99/59975; WO 99/59973; WO 99/11649; WO 99/11645; WO 99/11644; WO 99/11628; WO 99/11623; WO 99/11311; WO 00/42040; Zhang et al., Biochem. Biophys. Res. Commun., 278:590-98,2000; White et al., J. Med. Chem., 43:4084-4097, 2000; Griffin et al., J. Med. Chem., 41:5247-5256, 1998; Shinkwin et al., Bioorg. Med. Chem., 7:297-308, 1999; and Soriano et at., Nature Medicine, 7:108-113, 2001. Adverse effects associated with administration of PARS inhibitors have been discussed in Milan et al., Science, 223:589-591, 1984.

Isoquinoline compounds have been previously discussed in the art. For example, cytotoxic non-camptothecin topoisomerase I inhibitors are reported in Cushman et al., J. Med. Chem., 43:3688-3698, 2300 and Cushman et al., J. Med. Chem. 42:446-57, 1999; indeno[1,2-c]isoquinolines are reported as antineoplastic agents in Cushman et al., WO 00/21537; and as neoplasm inhibitors in Hrbata et al., WO 93/05023.

Syntheses of isoquinoline compounds have been reported. For example, see Wawzonek et al., Org. Prep. Proc. Int., 14:163-8, 1982; Wawzonek et al., Can. J. Chem., 59:2833, 1981; Andoi et al., Bull. Chem. Soc. Japan, 47:1014-17, 1974; Dusemund et al., Arch. Pharm (Weinheim, Ger.), 3 17:381-2, 1984; and Lal et al., Indian J. Chem., Sect. B, 38B:33-39, 1999.

There remains, however, a need in the art for compounds useful for treating or preventing an inflammatory disease, a reperfusion injury, diabetes, a diabetic complication, reoxygenation injury resulting from organ transplantation, an ischemic preventing condition, Parkinson's disease, renal failure, a vascular disease, a cardiovascular disease, or cancer.

Citation of any reference in Section 2 of this application is not an admission that the reference is prior art.

3. SUMMARY OF THE INVENTION

In one aspect the invention provides a compound of Formula (I)

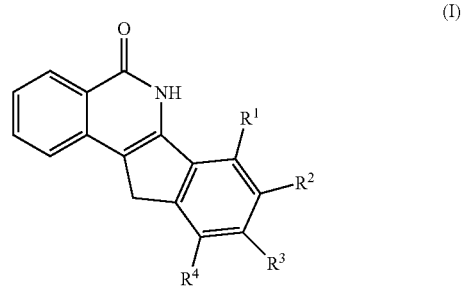

(I)

and pharmaceutically acceptable salts thereof wherein
one of the $R^1$, $R^2$, $R^3$ and $R^4$ groups is —NH(CH$_2$)$_n$—N(R$^5$)(R$^6$) and the remaining groups are simultaneously —H;

$R^5$ and $R^6$ are independently —H, —C$_1$-C$_6$ alkyl, -phenyl, or benzyl, wherein the —C$_1$-C$_6$ alkyl, -phenyl, or benzyl, is unsubstituted or substituted with one or more of -halo, —OH or —N(Z$_3$)(Z$_4$), where Z$_3$ and Z$_4$ are independently —H or —C$_1$-C$_5$ alkyl, which is unsubstituted or substituted with one or more of -halo, -hydroxy or —NH$_2$; or N, Z$_3$ and Z$_4$ are taken together to form an nitrogen-containing 3- to 7-membered monocyclic heterocycle which is unsubstituted or substituted with one to three of —C$_1$-C$_5$ alkyl, -halo, -halo-substituted C$_1$-C$_5$ alkyl, hydroxy, —O—C$_1$-C$_5$ alkyl, —N(R$^a$)$_2$, —COOH, —C(O)O—(C$_1$-C$_5$ alkyl), —OC(O)—(C$_1$-C$_5$ alkyl), —C(O)NH$_2$, or —NO$_2$, wherein each occurrence of R$^a$ is independently —H, -benzyl, or —C$_1$-C$_{10}$ alkyl; or N, R$^5$ and R$^6$ are taken together to form a nitrogen-containing 3- to 7-membered monocyclic heterocycle which is unsubstituted or substituted with one to three of —C$_1$-C$_5$ alkyl, phenyl, benzyl, hydroxy-substituted C$_1$-C$_5$ alkyl, -halo, -halo-substituted C$_1$-C$_5$ alkyl, halo-substituted phenyl, hydroxy, —O—C$_1$-C$_5$ alkyl, —(O—C$_1$-C$_5$-alkyl)-substituted phenyl, cyano-substituted phenyl, —N(R$^a$)$_2$, —(C$_1$-C$_5$ alkylene)-N(R$^a$)$_2$, —COOH, —(C$_1$-C$_5$ alkylene)-COOH, —(C$_1$-C$_5$ alkylene)-C(O)O—C$_1$-C$_5$ alkyl, —(C$_1$-C$_5$-alkylene)-C(O)NH—C$_1$-C$_5$ alkyl, —C(O)O—(C$_1$-C$_5$ alkyl), —OC(O)—(C$_1$-C$_5$ alkyl), —C(O)NH$_2$, or —NO$_2$, wherein each occurrence of R$^a$ is independently —H, -benzyl, or —C$_1$-C$_{10}$ alkyl; and n is an integer ranging from 2 to 6.

In another aspect the invention includes a compound of Formula (II)

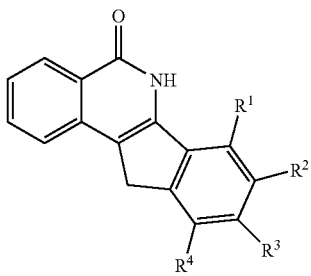

(II)

and pharmaceutically acceptable salts thereof wherein one of the $R^1$, $R^2$, $R^3$ and $R^4$ groups is —C(O)NH $(CH_2)_n$—$N(R^5)(R^6)$ and the remaining groups are simultaneously —H;

$R^5$ and $R^6$ are independently —H, —$C_1$-$C_6$ alkyl, -phenyl, or benzyl, wherein the —$C_1$-$C_6$ alkyl, -phenyl, or benzyl, is unsubstituted or substituted with one or more of -halo, —OH or —$N(Z_3)(Z_4)$, where $Z_3$ and $Z_4$ are independently —H or —$C_1$-$C_5$ alkyl, which is unsubstituted or substituted with one or more of -halo, -hydroxy or —$NH_2$; or N, $Z_3$ and $Z_4$ are taken together to form an nitrogen-containing 3- to 7-membered monocyclic heterocycle which is unsubstituted or substituted with one to three of —$C_1$-$C_5$ alkyl, -halo, -halo-substituted $C_1$-$C_5$ alkyl, hydroxy, —O—$C_1$-$C_5$ alkyl, —$N(R^a)_2$, —COOH, —C(O)O—($C_1$-$C_5$ alkyl), —OC(O)—($C_1$-$C_5$ alkyl), —C(O)$NH_2$, or N, $R^5$ and $R^6$ are taken together to form a nitrogen-containing 3- to 7-membered monocyclic heterocycle which is unsubstituted or substituted with one to three of —$C_1$-$C_5$ alkyl, phenyl, benzyl, hydroxy-substituted $C_1$-$C_5$ alkyl, -halo, -halo-substituted $C_1$-$C_5$ alkyl, halo-substituted phenyl, hydroxy, —O—$C_1$-$C_5$ alkyl, —(O—$C_1$-$C_5$-alkyl)-substituted phenyl, cyano-substituted phenyl, —$N(R^a)_2$, —($C_1$-$C_5$ alkylene)-$N(R^a)_2$, —COOH, —($C_1$-$C_5$ alkylene)-COOH, —($C_1$-$C_5$ alkylene)-C(O)O—$C_1$-$C_5$ alkyl, —($C_1$-$C_5$-alkylene)-C(O)NH—$C_1$-$C_5$ alkyl, —C(O)O—($C_1$-$C_5$ alkyl), —OC(O)—($C_1$-$C_5$ alkyl), —C(O)$NH_2$, or —$NO_2$, wherein each occurrence of $R^a$ is independently —H, -benzyl, or —$C_1$-$C_{10}$ alkyl; and n is an integer ranging from 2 to 6.

A Compound of Formula (I) or a pharmaceutically acceptable salt thereof (a "Tetracyclic Amino Compound") and a compound of Formula (II) or a pharmaceutically acceptable salt thereof (a "Tetracyclic Carboxamido Compound") are useful for treating or preventing an inflammatory disease, a reperfusion injury, diabetes, a diabetic complication, reoxygenation injury resulting from organ transplantation, an ischemic condition, Parkinson's disease, renal failure, a vascular disease, a cardiovascular disease, or cancer (each being a "Condition").

Also provided by the invention are methods for treating or preventing a Condition, comprising administering to a subject in need of such treatment or prevention an effective amount of a Tetracyclic Amino Compound.

The invention further provides compositions comprising and an effective amount of a Tetracyclic Amino Compound and a physiologically acceptable carrier or vehicle.

Also provided by the invention are methods for treating or preventing a Condition, comprising administering to a subject in need of such treatment or prevention an effective amount of a Tetracyclic Carboxamido Compound.

The invention provides compositions comprising and an effective amount of a Tetracyclic Carboxamido Compound and a physiologically acceptable carrier or vehicle.

The details of the invention are set forth in the accompanying description below.

Although any methods and materials similar or equivalent to those described herein can be used in the practice or testing of the present invention, illustrative methods and materials are now described. Other features, objects, and advantages of the invention will be apparent from the description and from the claims. All patents and publications cited in this specification are incorporated by reference.

4. DETAILED DESCRIPTION OF THE INVENTION 4.1 Definitions and Abbreviations

The following definitions are used in connection with the Tetracyclic Amino Compounds and the Tetracyclic Carboxamido Compounds:

The term "—$C_1$-$C_5$ alkyl" as used herein, refers to a straight chain or branched non-cyclic hydrocarbon having from 1 to 5 carbon atoms, wherein one of the hydrocarbon's hydrogen atoms has been replaced by a single bond. Representative straight chain —$C_1$-$C_5$ alkyls include -methyl, -ethyl, -n-propyl, -n-butyl and -n-pentyl. Representative branched —$C_1$-$C_5$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl.

The term "—$C_1$-$C_6$ alkyl" as used herein, refers to a straight chain or branched non-cyclic hydrocarbon having from 1 to 6 carbon atoms, wherein one of the hydrocarbon's hydrogen atoms has been replaced by a single bond. Representative straight chain —$C_1$-$C_6$ alkyls include -methyl, -ethyl, -n-propyl, -n-butyl, -n-pentyl and -n-hexyl. Representative branched —$C_1$-$C_6$ alkyls include -isopropyl, -sec-butyl, -isobutyl, -tert-butyl, -isopentyl, -neopentyl, -1-methylbutyl, -isohexyl, -neohexyl, -2-methylbutyl, -3-methylbutyl, -1,1-dimethylpropyl and -1,2-dimethylpropyl.

The term "—$C_1$-$C_{10}$ alkyl" as used herein, refers to a straight chain or branched non-cyclic hydrocarbon having from 1 to 10 carbon atoms, wherein one of the hydrocarbon's hydrogen atoms has been replaced by a single bond. Representative —$C_1$-$C_{10}$ alkyls include, methyl, ethyl, propyl, butyl, pentyl, hexyl, heptyl, octyl, -nonyl, decyl, isopropyl, isobutyl, sec-butyl and tert-butyl, isopentyl, neopentyl, isohexyl, isoheptyl, isooctyl, isononyl and isodecyl.

The term "—$C_1$-$C_5$ alkylene-" as used herein, refers to a straight chain or branched acylic hydrocarbon having from 1-5 carbon atoms, wherein two of the hydrocarbon's hydrogen atoms has been replaced by a single bond. Representative —$C_1$-$C_5$ alkylene-groups include methylene, ethylene, propylene, butylene, and pentylene. Other —$C_1$-$C_5$ alkylene-groups include —CH($CH_3$)—, —$CH_2$CH($CH_3$)—, —$CH_2CH_2$CH($CH_3$)—, —$CH_2$CH($CH_3$)$CH_2$—, —CH($CH_3$)CH($CH_3$)—, —$CH_2CH_2CH_2$CH($CH_3$)—, —$CH_2CH_2$CH($CH_3$)$CH_2$—, —CH($CH_3$)CH($CH_3$)$CH_2$— and —CH($CH_3$)$CH_2$CH($CH_3$)—.

A "nitrogen containing 3- to 7-membered monocyclic heterocycle" refers to a monocyclic 3- to 7-membered aromatic or non-aromatic monocyclic cycloalkyl group in which one of the cycloalkyl group's ring carbon atoms has been replaced with a nitrogen atom and 0-4 of the cycloalkyl group's remaining ring carbon atoms may be independently replaced with a N, O or S atom. The nitrogen containing 3- to 7-membered monocyclic heterocycles can be attached via a nitrogen, sulfur, or carbon atom. Representative examples of nitrogen-containing-3- to 7-membered monocyclic heterocycles include, but are not limited to, piperidinyl, piperazinyl, pyrrolyl, oxazinyl, thiazinyl, diazinyl, triazinyl, tetrazinyl, imidazolyl, tetrazolyl, pyrrolidinyl, isoxazolyl, pyridinyl, oxazolyl, thiazolyl, pyrazolyl, triazolyl, pyrimidinyl, and morpholinyl. In one embodiment, a nitrogen containing 3- to 7-membered monocyclic heterocycle is substituted with up to three groups, independently chosen from: —$C_1$-$C_5$ alkyl, -halo, -halo-substituted $C_1$-$C_5$ alkyl, hydroxy, —O—$C_1$-$C_5$ alkyl, —N($R^a$)$_2$, —COOH, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl.

"Halo" is —F, —Cl, —Br or —I.

A "subject" is a mammal, e.g., a human, mouse, rat, guinea pig, dog, cat, horse, cow, pig, or non-human primate, such as a monkey, chimpanzee, baboon or rhesus. In one embodiment, the subject is a human.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, butyrate, calcium edetate, camphorsulfonate, camsylate, carbonate, citrate, clavulariate, dihydrochloride, edetate, edisylate, estolate, esylate, fiunarate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A hydrate is another example of a pharmaceutically acceptable salt.

In one embodiment, the pharmaceutically acceptable salt is a mesylate salt.

In another embodiment, the pharmaceutically acceptable salt is a camphorsulfonate salt.

An "effective amount" when used in connection with a Tetracyclic Amino Compound or a Tetracyclic Carboxamido Compound is an amount that is effective for treating or preventing a Condition.

An "effective amount" when used in connection with another anticancer agent is an amount that is effective for treating or preventing cancer alone or in combination with a Tetracyclic Amino Compound or a Tetracyclic Carboxamido Compound. "In combination with" includes administration within the same composition and within separate compositions. In the latter instance, the anticancer agent is administered during a time when the Tetracyclic Amino Compound or the Tetracyclic Carboxamido Compound exerts its prophylactic or therapeutic effect, or vice versa.

4.2 The Tetracyclic Amino Compounds of Formula (I)

The present invention provides Tetracyclic Amino Compounds according to Formula (I), below:

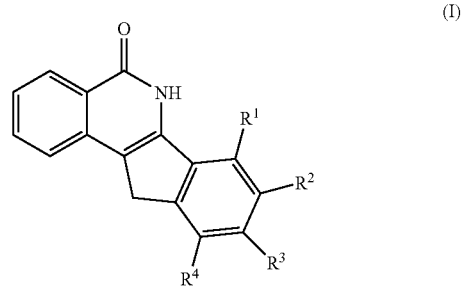

(I)

and pharmaceutically acceptable salts thereof, wherein:

$R^1$, $R^2$, $R^3$ and $R^4$ are as defined above for the compounds of formula (I).

In one embodiment, $R^1$ is —NH(CH$_2$)$_n$—N($R^5$)($R^6$) and $R^2$, $R^3$ and $R^4$ are each hydrogen.

In another embodiment, $R^2$ is —NH(CH$_2$)$_n$—N($R^5$)($R^6$) and $R^1$, $R^3$ and $R^4$ are each hydrogen.

In another embodiment, $R^3$ is —NH(CH$_2$)$_n$—N($R^5$)($R^6$) and $R^1$, $R^2$ and $R^4$ are each hydrogen.

In still another embodiment, $R^4$ is —NH(CH$_2$)$_n$—N($R^5$)($R^6$) and $R^1$, $R^2$ and $R^3$ are each hydrogen.

In another embodiment, n is 2.

In still another embodiment, n is 3.

In yet another embodiment, n is 4.

In a further embodiment, n is 5.

In another embodiment, n is 6.

In another embodiment N, $R^5$ and $R^6$ are taken together to form a nitrogen-containing 3- to 7-membered monocyclic heterocycle which is unsubstituted or substituted with one to three of —$C_1$-$C_5$ alkyl, -halo, -halo-substituted $C_1$-$C_5$ alkyl, hydroxy, —O—$C_1$-$C_5$ alkyl, —N($R^a$)$_2$, —COOH, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl.

In various embodiments, —N($R^5$)($R^6$) is:

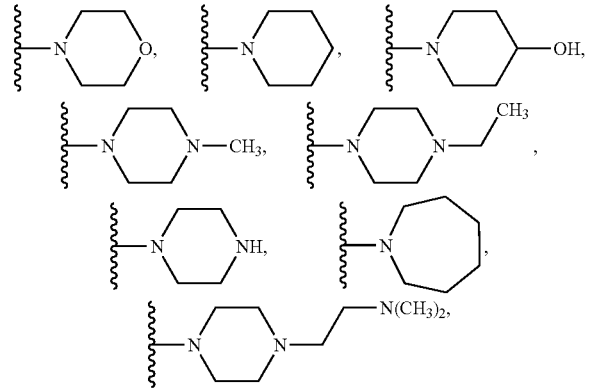

-continued

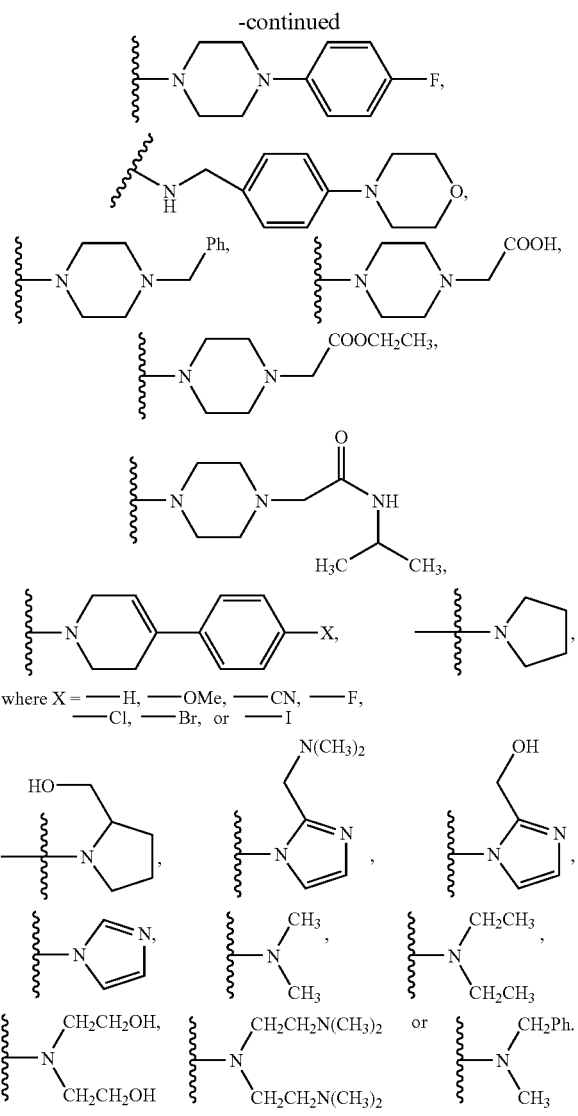

where X = —H, —OMe, —CN, —F,
—Cl, —Br, or —I

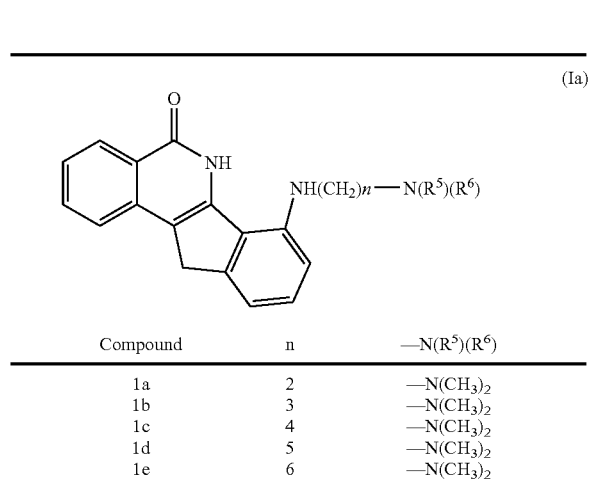

Illustrative examples of the Tetracyclic Amino Compounds of Formula (I) include the compounds of Formula (Ia) as set forth below:

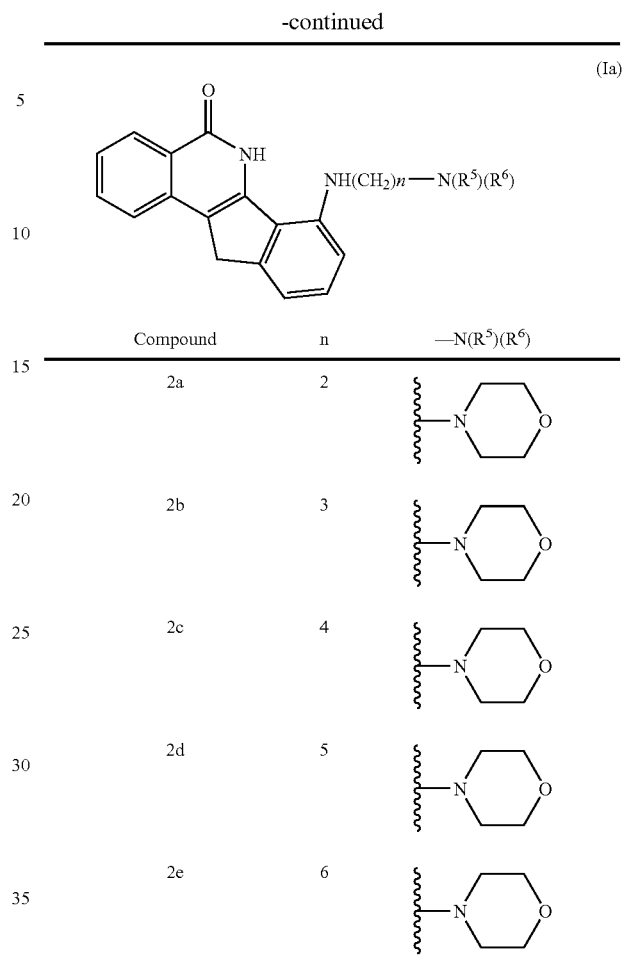

| Compound | n | —N($R^5$)($R^6$) |
|---|---|---|
| 2a | 2 | morpholine |
| 2b | 3 | morpholine |
| 2c | 4 | morpholine |
| 2d | 5 | morpholine |
| 2e | 6 | morpholine | and pharmaceutically acceptable salts thereof.

Other illustrative examples of the Tetracyclic Amino Compounds of Formula (I) include the compounds of Formula (Ib) as set forth below:

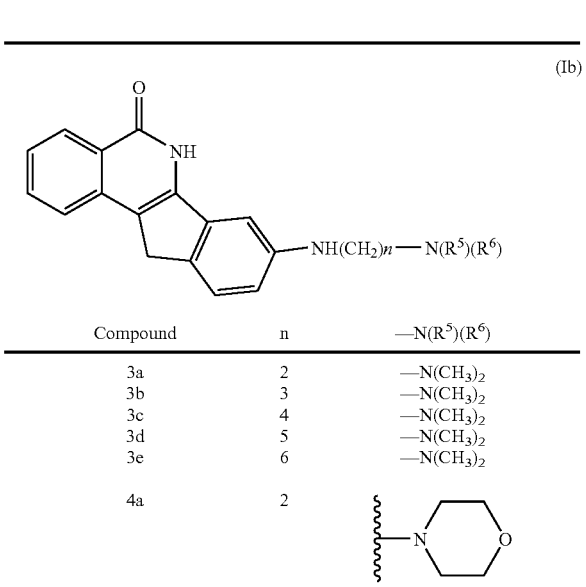

| Compound | n | —N($R^5$)($R^6$) |
|---|---|---|
| 3a | 2 | —N(CH$_3$)$_2$ |
| 3b | 3 | —N(CH$_3$)$_2$ |
| 3c | 4 | —N(CH$_3$)$_2$ |
| 3d | 5 | —N(CH$_3$)$_2$ |
| 3e | 6 | —N(CH$_3$)$_2$ |
| 4a | 2 | morpholine |

-continued (Ib)

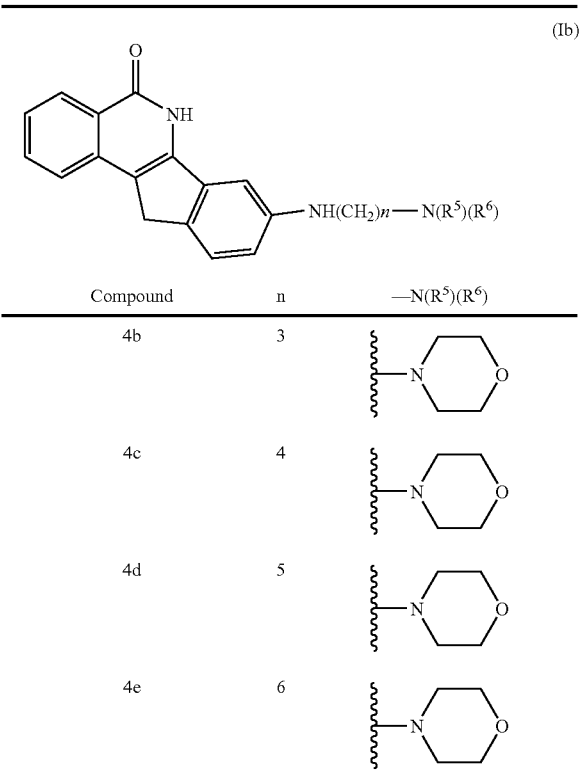

| Compound | n | —N(R⁵)(R⁶) |
|---|---|---|
| 4b | 3 | —N(morpholine) |
| 4c | 4 | —N(morpholine) |
| 4d | 5 | —N(morpholine) |
| 4e | 6 | —N(morpholine) | and pharmaceutically acceptable salts thereof.

Other illustrative examples of the Tetracyclic Amino Compounds of Formula (I) include the compounds of Formula (Ic) as set forth below:

(Ic)

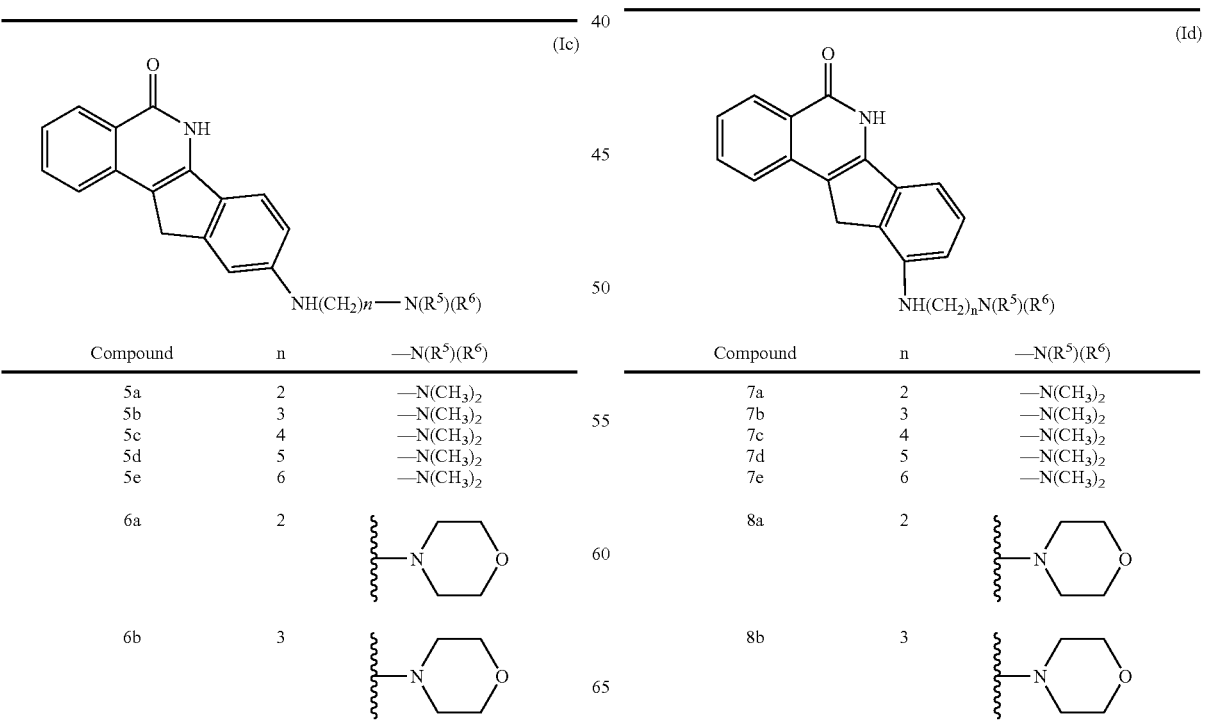

| Compound | n | —N(R⁵)(R⁶) |
|---|---|---|
| 5a | 2 | —N(CH$_3$)$_2$ |
| 5b | 3 | —N(CH$_3$)$_2$ |
| 5c | 4 | —N(CH$_3$)$_2$ |
| 5d | 5 | —N(CH$_3$)$_2$ |
| 5e | 6 | —N(CH$_3$)$_2$ |
| 6a | 2 | —N(morpholine) |
| 6b | 3 | —N(morpholine) |
| 6c | 4 | —N(morpholine) |
| 6d | 5 | —N(morpholine) |
| 6e | 6 | —N(morpholine) | and pharmaceutically acceptable salts thereof.

Other illustrative examples of the Tetracyclic Amino Compounds of Formula (I) include the compounds of Formula (Id) as set forth below:

(Id)

| Compound | n | —N(R⁵)(R⁶) |
|---|---|---|
| 7a | 2 | —N(CH$_3$)$_2$ |
| 7b | 3 | —N(CH$_3$)$_2$ |
| 7c | 4 | —N(CH$_3$)$_2$ |
| 7d | 5 | —N(CH$_3$)$_2$ |
| 7e | 6 | —N(CH$_3$)$_2$ |
| 8a | 2 | —N(morpholine) |
| 8b | 3 | —N(morpholine) |

-continued

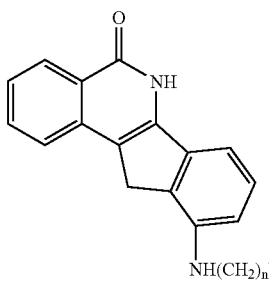

| Compound | n | —N(R⁵)(R⁶) |
|---|---|---|
| 8c | 4 | morpholine |
| 8d | 5 | morpholine |
| 8e | 6 | morpholine | and pharmaceutically acceptable salts thereof.

4.3 The Tetracyclic Carboxamido Compounds of Formula (II)

The present invention provides Tetracyclic Carboxamido Compounds according to Formula (II), below:

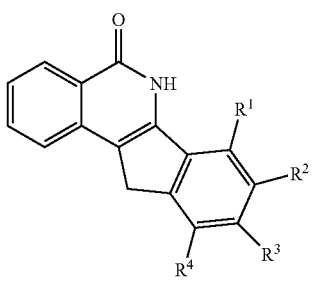

and pharmaceutically acceptable salts thereof,
wherein:
$R^1$, $R^2$, $R^3$ and $R^4$ are as defined above for the compounds of formula (II).

In one embodiment, $R^1$ is —C(O)NH—(CH$_2$)$_n$—N(R⁵)(R⁶) and $R^2$, $R^3$ and $R^4$ are each hydrogen.

In another embodiment, $R^2$ is —C(O)NH—(CH$_2$)$_n$—N(R⁵)(R⁶) and $R^1$, $R^3$ and $R^4$ are each hydrogen.

In another embodiment, $R^3$ is —C(O)NH—(CH$_2$)$_n$—N(R⁵)(R⁶) and $R^1$, $R^2$ and $R^4$ are each hydrogen.

In still another embodiment, $R^4$ is —C(O)NH—(CH$_2$)$_n$—N(R⁵)(R⁶) and $R^1$, $R^2$ and $R^3$ are each hydrogen.

In another embodiment, n is 2.
In still another embodiment, n is 3.
In yet another embodiment, n is 4.
In a further embodiment, n is 5.

In another embodiment N, R⁵ and R⁶ are taken together to form a nitrogen-containing 3- to 7-membered monocyclic heterocycle which is unsubstituted or substituted with one to three of —C$_1$-C$_5$ alkyl, -halo, -halo-substituted C$_1$-C$_5$ alkyl, hydroxy, —O—C$_1$-C$_5$ alkyl, —N(R$^a$)$_2$, —COOH, —C(O)O—(C$_1$-C$_5$ alkyl), —OC(O)—(C$_1$-C$_5$ alkyl), —C(O)NH$_2$, or —NO$_2$, wherein each occurrence of R$^a$ is independently —H, -benzyl, or —C$_1$-C$_{10}$ alkyl.

In various embodiments, —N(R⁵)(R⁶) is:

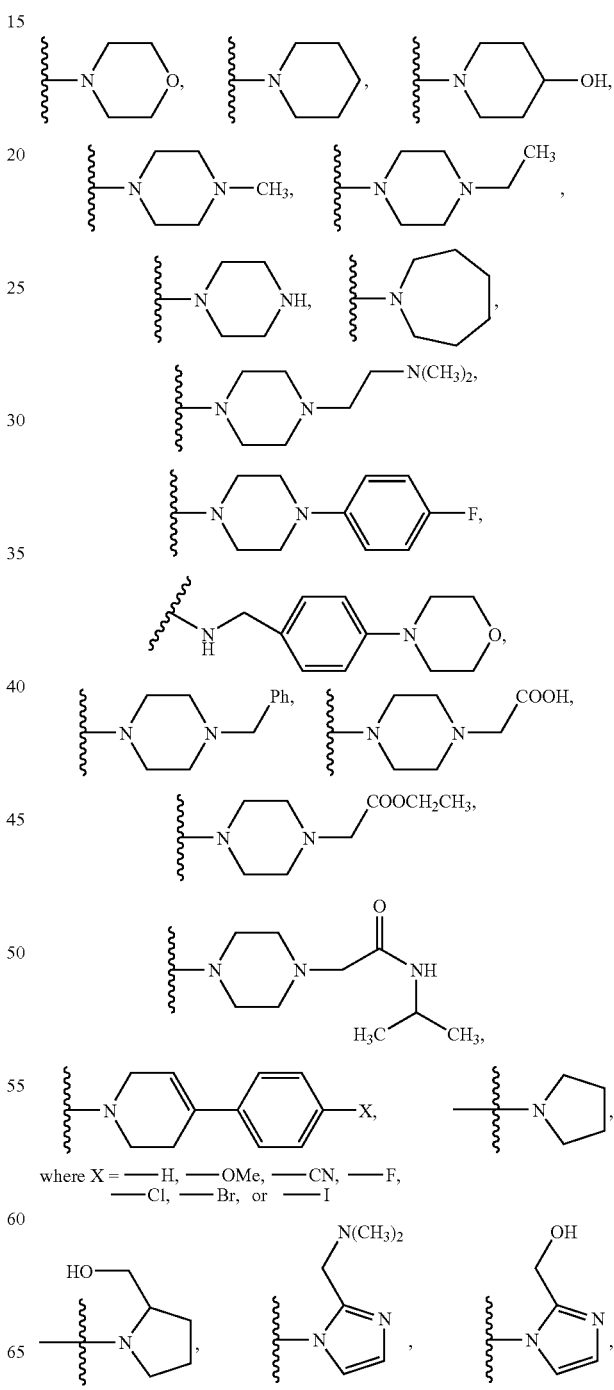

where X = —H, —OMe, —CN, —F, —Cl, —Br, or —I

-continued

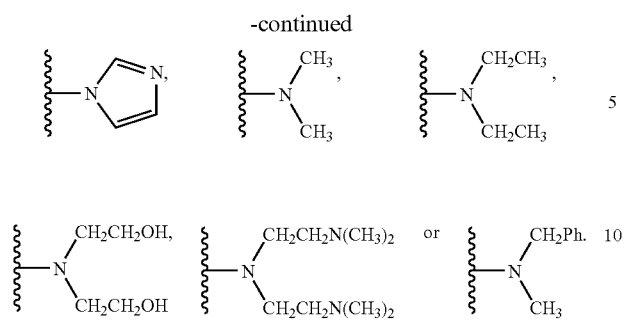

Illustrative examples of the Tetracyclic Carboxamido Compounds of Formula (II) include the compounds of Formula (IIa) as set forth below:

(IIa)

| Compound | n | —N(R⁵)(R⁶) |
|---|---|---|
| 9a | 2 | —N(CH₃)₂ |
| 9b | 3 | —N(CH₃)₂ |
| 9c | 4 | —N(CH₃)₂ |
| 9d | 5 | —N(CH₃)₂ |
| 10a | 2 | morpholino |
| 10b | 3 | morpholino |
| 10c | 4 | morpholino |
| 10d | 5 | morpholino | and pharmaceutically acceptable salts thereof.

Other illustrative examples of the Tetracyclic Carboxamido Compounds of Formula (II) include the compounds of Formula (IIb) as set forth below:

(IIb)

| Compound | n | —N(R⁵)(R⁶) |
|---|---|---|
| 11a | 2 | —N(CH₃)₂ |
| 11b | 3 | —N(CH₃)₂ |
| 11c | 4 | —N(CH₃)₂ |
| 11d | 5 | —N(CH₃)₂ |
| 12a | 2 | morpholino |
| 12b | 3 | morpholino |
| 12c | 4 | morpholino |
| 12d | 5 | morpholino | and pharmaceutically acceptable salts thereof.

Other illustrative examples of the Tetracyclic Carboxamido Compounds of Formula (II) include the compounds of Formula (IIc) as set forth below:

(IIc)

| Compound | n | —N(R⁵)(R⁶) |
|---|---|---|
| 13a | 2 | —N(CH₃)₂ |
| 13b | 3 | —N(CH₃)₂ |
| 13c | 4 | —N(CH₃)₂ |
| 13d | 5 | —N(CH₃)₂ |
| 14a | 2 | 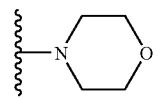 |

-continued (IIc)

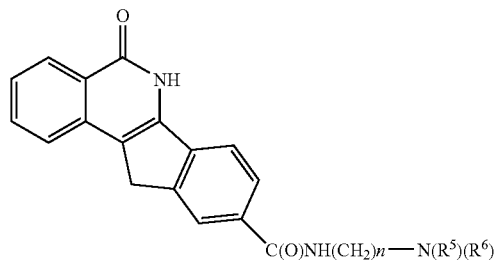

| Compound | n | —N(R⁵)(R⁶) |
|---|---|---|
| 14b | 3 | 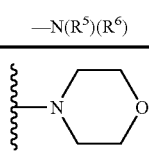 |
| 14c | 4 | 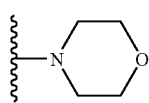 |
| 14d | 5 | 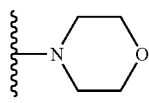 | and pharmaceutically acceptable salts thereof.

Other illustrative examples of the Tetracyclic Carboxamido Compounds of Formula (II) include the compounds of Formula (IId) as set forth below:

(IId)

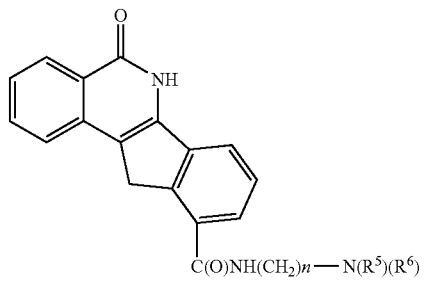

| Compound | n | —N(R⁵)(R⁶) |
|---|---|---|
| 15a | 2 | —N(CH₃)₂ |
| 15b | 3 | —N(CH₃)₂ |
| 15c | 4 | —N(CH₃)₂ |
| 15d | 5 | —N(CH₃)₂ |

-continued (IId)

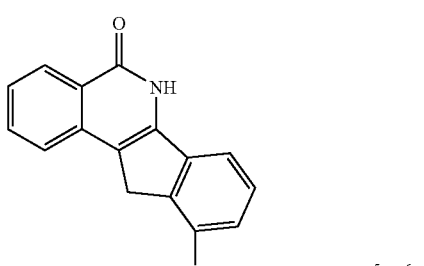

| Compound | n | —N(R⁵)(R⁶) |
|---|---|---|
| 16a | 2 | 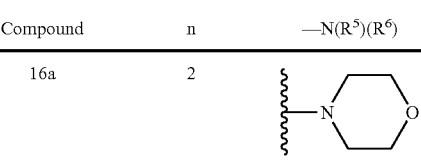 |
| 16b | 3 | 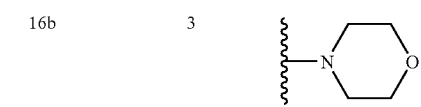 |
| 16c | 4 |  |
| 16d | 5 | 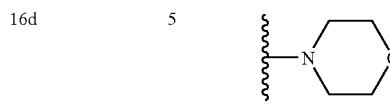 | and pharmaceutically acceptable salts thereof.

4.4 Methods for Making the Tetracyclic Amino Compounds or the Tetracyclic Carboxamido Compounds Methods useful for making the Tetracyclic Amino Compounds and the Tetracyclic Carboxamido Compounds are set forth in the Examples below and generalized in Schemes 1-4.

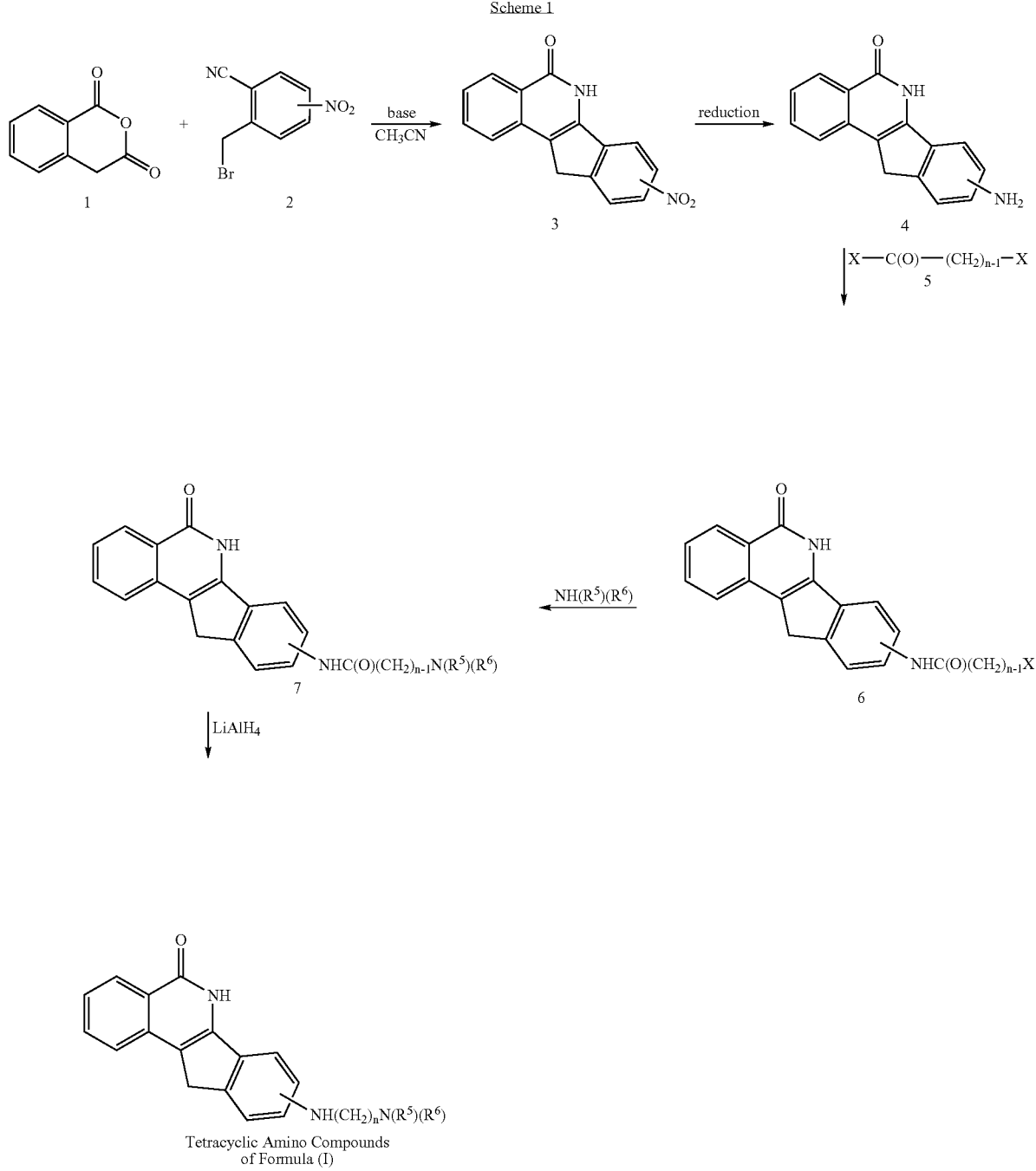

Scheme 1

Tetracyclic Amino Compounds of Formula (I)

wherein each X is independently —Cl or —Br, and n, $R^5$ and $R^6$ are defined above for the Compounds of Formula (I).

Homophthalic anhydride 1 can be coupled with a nitrobenzene compound of formula 2 in the presence of a base, for example, an amine base, to provide a tetracyclic nitro intermediate of formula 3. The nitro group of 3 can be reduced using, for example, catalytic hydrogenation with a platinum or palladium catalyst, to provide an amino compound of formula 4. A compound of formula 4 can then be reacted with a stoichometric excess of an acid halide compound of formula 5 to provide an amido compound of formula 6. The chlorine or bromine atom of 6 can then be displaced by an amine of formula $NH(R^5)(R^6)$ to provide an amino compound of formula 7. Finally, the amide moiety of a compound of formula 7 can be reduced using lithium aluminum hydride to provide the Tetracyclic Amino Compounds of Formula (I).

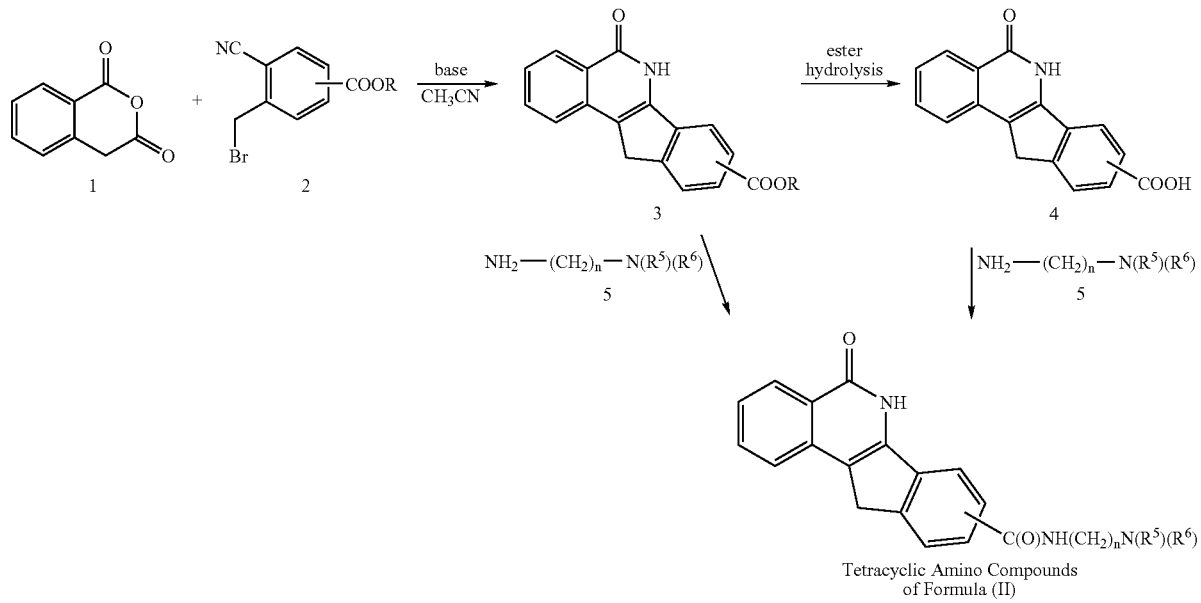

Tetracyclic Amino Compounds
of Formula (II)

wherein R is methyl or ethyl, and n, $R^5$ and $R^6$ are defined above for the Compounds of Formula (II).

Homophthalic anhydride 1 can be coupled with a phenylester compound of formula 2 in the presence of a base, for example, an amine base, to provide a tetracyclic nitro intermediate of formula 3. The ester group of 3 can be hydrolyzed under basic or acidic conditions to provide an carboxylic acid compound of formula 4. A compound of formula 3 or formul 4 can then be coupled with a diaminoalkyl compound of formula 5 (which is commercially available, or can be prepared by reacting dihaloalkyl compounds with various amines using methods well known to one of skill in the art of organic synthesis) to provide the Tetracyclic Carboxamido Compounds of Formula (II).

wherein n, $R^5$ and $R^6$ are defined as above for compounds of formula (IIc).

Compounds of Formula (IIc) can be made according to the general procedure of Scheme 3. Bromocarboxylic acid 1 can be reacted with methanol and sulfuric acid under reflux to give the bromo ester 2. The bromo ester 2 can be converted to the cyano ester 3 using, for example, Pd(OAc)$_2$ and K$_4$[Fe(CN)$_6$]. Treatment of compound 3 with N-bromosuccinamide and benzoyl peroxide provides bromobenzyl compound 4. Reaction of compound 4 with homophthalic anhydride in acetonitrile provides the fused ring structure of compound 5. Hydrolysis of the ester of compound 5 followed by addition of a coupling agent and the desired amine

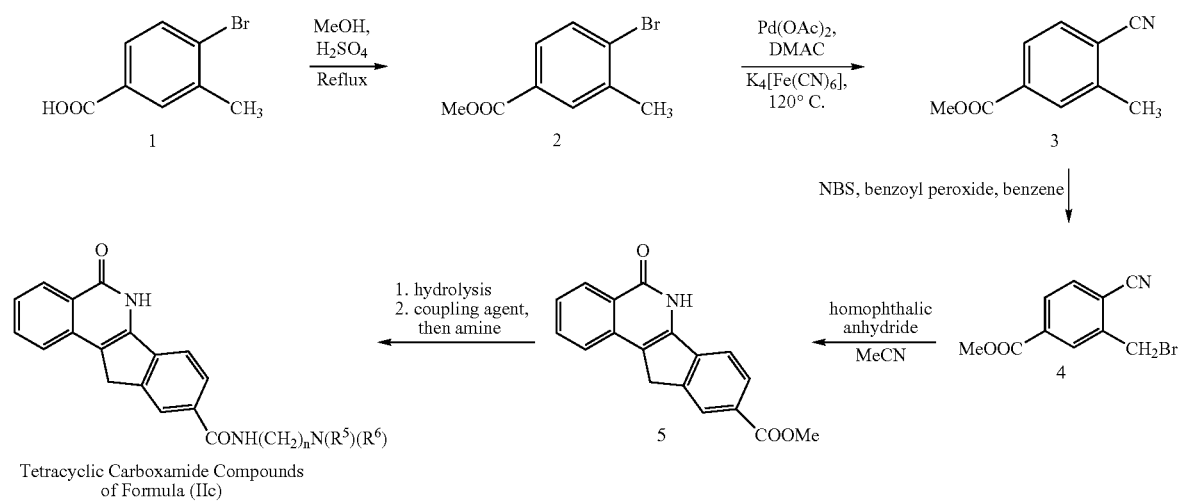

Tetracyclic Carboxamide Compounds
of Formula (IIc)

provides the Tetracyclic Carboxamido Compounds of Formula (IIc).

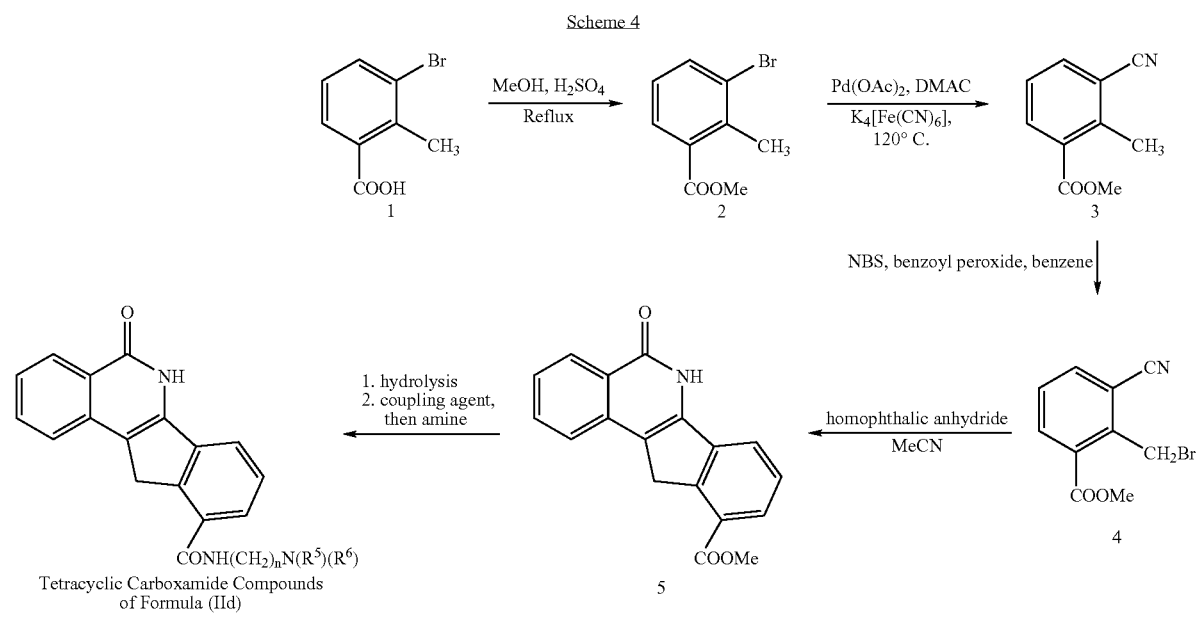

Scheme 4 wherein n, $R^5$ and $R^6$ are defined as above for compounds of formula (IId).

Compounds of Formula (IId) can be made according to the general procedure of Scheme 4. Bromocarboxylic acid 1 can be reacted with methanol and sulfuric acid under reflux to give the bromo ester 2. The bromo ester 2 can be converted to the cyano ester 3 using, for example, $Pd(OAc)_2$ and $K_4[Fe(CN)_6]$. Treatment of compound 3 with N-bromosuccinamide and benzoyl peroxide provides bromobenzyl compound 4. Reaction of compound 4 with homophthalic anhydride in acetonitrile provides the fused ring structure of compound 5. Hydrolysis of the ester of compound 5 followed by addition of a coupling agent and the desired amine provides the Tetracyclic Carboxamido Compounds of Formula (IId).

4.5 Uses of the Tetracyclic Amino Compounds or the Tetracyclic Carboxamido Compounds In accordance with the invention, the Tetracyclic Amino Compounds or the Tetracyclic Carboxamido Compounds are administered to a subject in need of treatment or prevention of a Condition.

4.5.1 Treatment or Prevention of an Inflammatory Disease

The Tetracyclic Amino Compounds or the Tetracyclic Carboxamido Compounds can be used to treat an inflammatory disease. Inflammatory diseases can arise where there is an inflammation of the body tissue. These include local inflammatory responses and systemic inflammation. Examples of inflammatory diseases treatable or preventable using the Tetracyclic Amino Compounds or the Tetracyclic Carboxamido Compounds include, but are not limited to, organ transplant rejection; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimers disease, infectious meningitis, encephalomyelitis, Huntington's disease, amyotrophic lateral sclerosis and viral or autoimmune encephalitis; as well as various other diseases that can have significant inflammatory components, including preeclampsia, chronic liver failure, and brain and spinal cord trauma. The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

In one embodiment, the inflammatory disease is the inflammatory disease is an inflammatory disease of a joint, a chronic inflammatory disease of the gum, an inflammatory bowel disease, an inflammatory lung disease, an inflammatory disease of the central nervous system, an inflammatory disease of the eye, gram-positive shock, gram negative shock, hemorrhagic shock, anaphylactic shock, traumatic shock or chemotherapeutic shock.

4.5.2 Treatment or Prevention of a Reperfusion Injury

The Tetracyclic Amino Compounds or the Tetracyclic Carboxamido Compounds can be used to treat a reperfusion injury. Reperfusion refers to the process whereby blood flow in the blood vessels is resumed following ischemia, such as occurs following constriction or obstruction of the vessel. Reperfusion injury can result following a naturally occurring episode, such as a myocardial infarction, stroke, or during a surgical procedure where blood flow in vessels is intentionally or unintentionally blocked. Examples of reperfusion injuries treatable or preventable using the Tetracyclic Amino Compounds or the Tetracyclic Carboxamido Compounds include, but are not limited to, intestinal reperfusion injury, myocardial reperfusion injury, and reperfusion injury resulting from cardiopulmonary bypass surgery, aortic aneurysm repair surgery, carotid endarterectomy surgery, or hemorrhagic shock.

In one embodiment, the reperfusion injury results from cardiopulmonary bypass surgery, aortic aneurysm repair surgery, carotid endarterectomy surgery or hemorrhagic shock.

4.5.3 Treatment or Prevention of Reoxygenation Injury Resulting from Organ Transplantation The Tetracyclic Amino Compounds or the Tetracyclic Carboxamido Compounds can be used to treat or prevent reoxygenation injury resulting from organ transplantation. Examples of reoxygenation injuries treatable or preventable using the Tetracyclic Amino Compounds or the Tetracyclic Carboxamido Compounds include, but are not limited to, transplantation of the following organs: heart, lung, liver, kidney, pancreas, intestine and cornea.

In one embodiment, reoxygenation injury resulting from organ transplantation occurs during the organ transplantation.

4.5.4 Treatment or Prevention of an Ischemic Condition

The Tetracyclic Amino Compounds or the Tetracyclic Carboxamido Compounds can be used to treat or prevent an ischemic condition. Examples of ischemic conditions treatable or preventable using the Tetracyclic Amino Compounds or the Tetracyclic Carboxamido Compounds include, but are not limited to, stable angina, unstable angina, myocardial ischemia, hepatic ischemia, mesenteric artery ischemia, ischemic heart disease, intestinal ischemia, critical limb ischemia, chronic critical limb ischemia, cerebral ischemia, acute cardiac ischemia, and an ischemic disease of the central nervous system, such as stroke or cerebral ischemia.

In one embodiment, the ischemic condition is myocardial ischemia, stable angina, unstable angina, stroke, ischemic heart disease or cerebral ischemia.

4.5.5 Treatment or Prevention of Renal Failure

The Tetracyclic Amino Compounds or the Tetracyclic Carboxamido Compounds can be used to treat or prevent renal failure.

In one embodiment, the renal failure is chronic renal failure.

In another embodiment, the renal failure is acute renal failure.

4.5.6 Treatment or Prevention of a Vascular Disease

The Tetracyclic Amino Compounds or the Tetracyclic Carboxamido Compounds can be used to treat or prevent a vascular disease other than a cardiovascular disease. Examples of vascular diseases treatable or preventable using the Tetracyclic Amino Compounds or the Tetracyclic Carboxamido Compounds include, but are not limited to, peripheral arterial occlusion, thromboangitis obliterans, Reynaud's disease and phenomenon, acrocyanosis, erythromelalgia, venous thrombosis, varicose veins, arteriovenous fistula, lymphedema, and lipedema.

4.5.7 Treatment or Prevention of a Cardiovascular Disease

The Tetracyclic Amino Compounds or the Tetracyclic Carboxamido Compounds can be used to treat or prevent a cardiovascular disease. Examples of cardiovascular diseases treatable or preventable using the Tetracyclic Amino Compounds or the Tetracyclic Carboxamido Compounds include, but are not limited to, chronic heart failure, atherosclerosis, congestive heart failure, hypercholesterolemia, circulatory shock, cardiomyopathy, cardiac transplant, myocardial infarction, and a cardiac arrhythmia, such as atrial fibrillation, supraventricular tachycardia, atrial flutter, and paroxysmal atrial tachycardia.

In one embodiment, the cardiovascular disease is chronic heart failure.

In another embodiment, the cardiovascular disease is a cardiac arrhythmia.

In still another embodiment, the cardiac arrhythmia is atrial fibrillation, supraventricular tachycardia, atrial flutter or paroxysmal atrial tachycardia.

4.5.8 Treatment or Prevention of Diabetes or a Diabetic Complication

The Tetracyclic Amino Compounds or the Tetracyclic Carboxamido Compounds can be used to treat or prevent diabetes mellitus or its complications. Examples of diabetes mellitus that are treatable or preventable using the Tetracyclic Amino Compounds or the Tetracyclic Carboxamido Compounds include, but are not limited to, Type I diabetes (Insulin Dependent Diabetes Mellitus), Type II diabetes (Non-Insulin Dependent Diabetes Mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by β-cell toxins.

The Tetracyclic Amino Compounds or the Tetracyclic Carboxamido Compounds can also be used to treat or prevent a complication of diabetes mellitus. Examples of complications of diabetes mellitus that are treatable or preventable using the Tetracyclic Amino Compounds or the Tetracyclic Carboxamido Compounds include, but are not limited to, diabetic cataract, glaucoma, retinopathy, nephropathy, (such as microaluminuria and progressive diabetic nephropathy), polyneuropathy, gangrene of the feet, immune-complex vasculitis, systemic lupus erythematosus (SLE), atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication (such as an infection, a shin spot, a candidal infection or necrobiosis lipoidica diabeticorumobesity), hyperlipidemia, hypertension, syndrome of insulin resistance, coronary artery disease, retinopathy, diabetic neuropathy, polyneuropathy, mononeuropathies, autonomic neuropathy, a foot ulcer, a joint problem, a fungal infection, cardiomyopathy, and a bacterial infection.

4.5.9 Treatment or Prevention of Parkinson's Disease

The Tetracyclic Amino Compounds or the Tetracyclic Carboxamido Compounds can be used to treat or prevent Parkinson's disease.

4.5.10 Treatment or Prevention of Cancer

The Tetracyclic Amino Compounds or the Tetracyclic Carboxamido Compounds can be used to treat or prevent cancer.

The invention provides methods for treating or preventing cancer, comprising administering to a subject in need of such treatment or prevention: (i) an effective amount of a Tetracyclic Amino Compound; and (ii) an effective amount of another anticancer agent.

The invention further provides methods for treating or preventing cancer, comprising administering to a subject in need of such treatment or prevention: (i) an effective amount of a Tetracyclic Carboxamido Compound; and (ii) an effective amount of the other anticancer agent.

Examples of cancers treatable or preventable using the Tetracyclic Amino Compounds or the Tetracyclic Carboxamido Compounds include, but are not limited to, the cancers disclosed below in Table 1 and metastases thereof.

TABLE 1

Solid tumors, including but not limited to:

fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon cancer
colorectal cancer
kidney cancer
pancreatic cancer
bone cancer
breast cancer
ovarian cancer
prostate cancer
esophageal cancer
stomach cancer
oral cancer
nasal cancer
throat cancer
squamous cell carcinoma
basal cell carcinoma
adenocarcinoma
sweat gland carcinoma
sebaceous gland carcinoma TABLE 1-continued papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma
skin cancer
melanoma
metastatic melanoma
neuroblastoma
retinoblastoma
blood-borne cancers, including but not limited to:

acute lymphoblastic leukemia ("ALL")
acute lymphoblastic B-cell leukemia
acute lymphoblastic T-cell leukemia
acute myeloblastic leukemia ("AML")
acute promyelocytic leukemia ("APL")
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia ("CML")
chronic lymphocytic leukemia ("CLL")
hairy cell leukemia
multiple myeloma
acute and chronic leukemias:

lymphoblastic
myelogenous
lymphocytic
myelocytic leukemias
Lymphomas:

Hodgkin's disease
non-Hodgkin's Lymphoma
Multiple myeloma
Waldenström's macroglobulinemia
Heavy chain disease
Polycythemia vera
Central nervous system lymphomas
CNS and Brain cancers:

glioma
pilocytic astrocytoma
astrocytoma
anaplastic astrocytoma
glioblastoma multiforme
medulloblastoma
craniopharyngioma
ependymoma
pinealoma
hemangioblastoma
acoustic neuroma
oligodendroglioma
meningioma
vestibular schwannoma
adenoma
metastatic brain tumor
meningioma
spinal tumor
medulloblastoma In one embodiment the cancer is lung cancer, breast cancer, colorectal cancer, prostate cancer, a leukemia, a lymphoma, non-Hodgkin's lymphoma, skin cancer, a brain cancer, a cancer of the central nervous system, ovarian cancer, uterine cancer, stomach cancer, pancreatic cancer, esophageal cancer, kidney cancer, liver cancer, or a head and neck cancer.

In another embodiment the cancer is metastatic cancer.

In still another embodiment, the subject in need of treatment has previously undergone or is presently undergoing treatment for cancer. The treatment includes, but is not limited to, prior chemotherapy, radiation therapy, surgery or immunotherapy, such as administration of cancer vaccines.

The Tetracyclic Amino Compound or the Tetracyclic Carboxamido Compounds are also useful for the treatment or prevention of a cancer caused by a virus. Such viruses include human papilloma virus, which can lead to cervical cancer (see, e.g., Hemandez-Avila et al., Archives of Medical Research (1997) 28:265-271); Epstein-Barr virus (EBV), which can lead to lymphoma (see, e.g., Herrmann et al., J Pathol (2003) 199(2):140-5); hepatitis B or C virus, which can lead to liver carcinoma (see, e.g., El-Serag, J Clin Gastroenterol (2002) 35(5 Suppl 2):S72-8); human T cell leukemia virus (HTLV)-I, which can lead to T-cell leukemia (see e.g., Mortreux et al., Leukemia (2003) 17(1):26-38); human herpesvirus-8 infection, which can lead to Kaposi's sarcoma (see, e.g., Kadow et al., Curr Opin Investig Drugs (2002) 3(11):1574-9); and Human Immune deficiency Virus (HIV) infection, which can lead to cancer as a consequence of immunodeficiency (see, e.g., Dal Maso et al., Lancet Oncol (2003) 4(2):110-9).

4.5.10.1 Prophylactic Methods for Cancer

The Tetracyclic Amino Compounds or the Tetracyclic Carboxamido Compounds can also be administered to prevent the progression of a cancer, including but not limited to the cancers listed in Table 1. Such prophylactic use includes that in which non-neoplastic cell growth consisting of hyperplasia, metaplasia, or most particularly, dysplasia has occurred.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic or therapeutic administration of a Tetracyclic Amino Compound or a Tetracyclic Carboxamido Compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are treatable or preventable according to the present methods.

In another embodiment, fibrocystic disease (cystic hyperplasia, mammary dysplasia, particularly adenosis (benign epithelial hyperplasia)) are treatable or preventable according to the present methods.

In other embodiments, a subject that has one or more of the following predisposing factors for malignancy can be treated by administration of an effective amount of a Tetracyclic Amino Compound or a Tetracyclic Carboxamido Compound: a chromosomal translocation associated with a malignancy (e.g., the Philadelphia chromosome for chronic myelogenous leukemia; t(14;18) for follicular lymphoma); familial polyposis or Gardner's syndrome; benign monoclonal gammopathy; a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; and exposure to carcinogens (e.g., smoking, secondhand smoke exposure, and inhalation of or contacting with certain chemicals).

4.5.10.2 Combination Chemotherapy for the Treatment of Cancer

In one aspect, the present methods for treating or preventing cancer can further comprise the administration of another anticancer agent.

In one embodiment, the present invention provides methods for treating or preventing cancer, comprising the administration of an effective amount of the following to a subject in need thereof: (i) a Tetracyclic Amino Compound and (ii) another anticancer agent.

In another embodiment, the present invention provides methods for treating or preventing cancer in a subject, the method comprising the administration of an effective amount of the following to a subject in need thereof: (i) a Tetracyclic Carboxamido Compound and (ii) another anticancer agent.

The (i) Tetracyclic Amino Compound or Tetracyclic Carboxamide Compound and (ii) other anticancer agent can be administered concurrently. In this embodiment the (i) Tetracyclic Amino Compound or Tetracyclic Carboxamide Compound and (ii) other anticancer agent can be administered within the same composition, or can be administered from different compositions, via the same or different routes of administration.

In another embodiment, the Tetracyclic Amino Compound or Tetracyclic Carboxamide Compound is administered during a time when the other anticancer agent exerts its prophylactic or therapeutic effect, or vice versa.

In one embodiment, the Tetracyclic Amino Compound or other anticancer agent are administered in doses commonly employed when such agents are used as monotherapy for the treatment of cancer.

In another embodiment, the Tetracyclic Carboxamido Compound or other anticancer agent are administered in doses commonly employed when such agents are used as monotherapy for the treatment of cancer.

In one embodiment, the Tetracyclic Amino Compound or other anticancer agent are administered in doses that are lower than the doses commonly employed when such agents are used as monotherapy for the treatment of cancer.

In another embodiment, the Tetracyclic Carboxamido Compound or other anticancer agent are administered in doses that are lower than the doses commonly employed when such agents are used as monotherapy for the treatment of cancer.

In one embodiment, the Tetracyclic Amino Compound and other anticancer agent act synergistically and are administered in doses that are lower than the doses commonly employed when such agents are used as monotherapy for the treatment of cancer.

In another embodiment the Tetracyclic Carboxamido Compound and other anticancer agent act synergistically and are administered in doses that are lower than the doses commonly employed when such agents are used as monotherapy for the treatment of cancer.

The dosage of the Tetracyclic Amino Compound or other anticancer agent administered as well as the dosing schedule can depend on various parameters, including, but not limited to, the cancer being treated, the subject's general health, and the administering physician's discretion.

The dosage of the Tetracyclic Carboxamido Compound or other anticancer agent administered as well as the dosing schedule can depend on various parameters, including, but not limited to, the cancer being treated, the subject's general health, and the administering physician's discretion.

A Tetracyclic Amino Compound or a Tetracyclic Carboxamido Compound can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent, to a subject in need thereof. In various embodiments a (i) Tetracyclic Amino Compound or a Tetracyclic Carboxamido Compound and (ii) the other anticancer agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, a (i) Tetracyclic Amino Compound or a Tetracyclic Carboxamido Compound and (ii) the other anticancer agent are administered within 3 hours. In another embodiment, a (i) Tetracyclic Amino Compound or a Tetracyclic Carboxamido Compound and (ii) the other anticancer agent are administered at 1 minute to 24 hours apart.

In one embodiment, an effective amount of a Tetracyclic Amino Compound and an effective amount of another anticancer agent are present in the same composition. In one embodiment, this composition is useful for oral administration. In another embodiment, this composition is useful for intravenous administration.

In one embodiment, an effective amount of a Tetracyclic Carboxamido Compound and an effective amount of another anticancer agent are present in the same composition. In one embodiment, this composition is useful for oral administration. In another embodiment, this composition is useful for intravenous administration.

Cancers that can be treated or prevented by administering a (i) Tetracyclic Amino Compound or a Tetracyclic Carboxamido Compound and (ii) the other anticancer agent include, but are not limited to, the list of cancers set forth above in Table 1.

In one embodiment, the cancer is brain cancer.

In specific embodiments, the brain cancer is pilocytic astrocytoma, astrocytoma, anaplastic astrocytoma, glioblastoma multiforme or a metastatic brain tumor.

In one embodiment, the cancer is melanoma.

In a specific embodiment, the melanoma is metastatic melanoma.

The (i) Tetracyclic Amino Compound or Tetracyclic Carboxamido Compound and (ii) other anticancer agent, can act additively or synergistically. A synergistic combination of a (i) Tetracyclic Amino Compound or a Tetracyclic Carboxamido Compound and (ii) the other anticancer agent, might allow the use of lower dosages of one or both of these agents and/or less frequent administration of the agents to a subject with cancer. The ability to utilize lower dosages of one or both of the (i) Tetracyclic Amino Compound or Tetracyclic Carboxamido Compound and (ii) other anticancer agent and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

In one embodiment, the (i) Tetracyclic Amino Compound or Tetracyclic Carboxamido Compound and (ii) one or more other anticancer agents act synergistically when administered in doses typically employed when such agents are used as monotherapy for the treatment of cancer. In another embodiment, the (i) Tetracyclic Amino Compound or Tetracyclic Carboxamido Compound and (ii) one or more other anticancer agents act synergistically when administered in doses that are lower than doses typically employed when such agents are used as monotherapy for the treatment of cancer.

In one embodiment, the administration of an effective amount of (i) a Tetracyclic Amino Compound or Tetracyclic Carboxamido Compound and (ii) an effective amount of another anticancer agent inhibits the resistance of a cancer to the other anticancer agent. In one embodiment, the cancer is a tumor.

Suitable other anticancer agents useful in the methods and compositions of the present invention include, but are not limited to temozolomide, a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, taxanes such as docetaxel and paclitaxel, leucovorin, levamisole, irinotecan, estramustine, etoposide, nitrogen mustards, BCNU, nitrosoureas such as carmustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins herbimycin A, genistein, erbstatin, and lavendustin A.

In one embodiment, the other anticancer agent is, but is not limited to, a drug listed in Table 2.

TABLE 2

| Alkylating agents | |
|---|---|
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| | Procarbazine |
| | Temozolomide |
| Platinum containing complexes: | Cisplatin |
| | Carboplatin |
| | Aroplatin |
| | Oxaliplatin |

Plant Alkaloids

| | |
|---|---|
| Vinca alkaloids: | Vincristine |
| | Vinblastine |
| | Vindesine |
| | Vinorelbine |
| Taxoids: | Paclitaxel |
| | Docetaxel |

DNA Topoisomerase Inhibitors

| | |
|---|---|
| Epipodophyllins: | Etoposide |
| | Teniposide |
| | Topotecan |
| | 9-aminocamptothecin |
| | Camptothecin |
| | Crisnatol |
| Mitomycins: | Mitomycin C |
| | Anti-metabolites |

Anti-folates:

| | |
|---|---|
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonuclotide reductase Inhibitors: | Hydroxyurea |
| | Deferoxamine |

Pyrimidine analogs:

| | |
|---|---|
| Uracil analogs: | 5-Fluorouracil |
| | Fluoxuridine |
| | Doxifluridine |
| | Ralitrexed |
| Cytosine analogs: | Cytarabine (ara C) |
| | Cytosine arabinoside |
| | Fludarabine |
| | Gemcitabine |
| | Capecitabine |
| Purine analogs: | Mercaptopurine |
| | Thioguanine |
| DNA Antimetabolites: | 3-HP |
| | 2'-deoxy-5-fluorouridine |
| | 5-HP |
| | alpha-TGDR |
| | aphidicolin glycinate |
| | ara-C |
| | 5-aza-2'-deoxycytidine |
| | beta-TGDR |
| | cyclocytidine |
| | guanazole |
| | inosine glycodialdehyde |
| | macebecin II |
| | Pyrazoloimidazole |

Hormonal therapies:

Receptor antagonists:

| | |
|---|---|
| Anti-estrogen: | Tamoxifen |
| | Raloxifene |
| | Megestrol |

TABLE 2-continued

| | |
|---|---|
| LHRH agonists: | Goserelin |
| | Leuprolide acetate |
| Anti-androgens: | Flutamide |
| | Bicalutamide |

Retinoids/Deltoids

| | |
|---|---|
| Vitamin A derivative: | Cis-retinoic acid |
| | All-trans retinoic acid (ATRA-IV) |
| Vitamin D3 analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A (2BA-2-DMHA) |
| Cytokines: | Interferon-α |
| | Interferon-β |
| | Interferon-γ |
| | Tumor necrosis factor |
| | Interleukin-2 |
| Angiogenesis Inhibitors: | Angiostatin (plasminogen fragment) |
| | antiangiogenic antithrombin III |
| | Angiozyme |
| | ABT-627 |
| | Bay 12-9566 |
| | Benefin |
| | Bevacizumab |
| | BMS-275291 |
| | cartilage-derived inhibitor (CDI) |
| | CAI |
| | CD59 complement fragment |
| | CEP-7055 |
| | Col 3 |
| | Combretastatin A-4 |
| | Endostatin (collagen XVIII fragment) |
| | Fibronectin fragment |
| | Gro-beta |
| | Halofuginone |
| | Heparinases |
| | Heparin hexasaccharide fragment |
| | HMV833 |
| | Human chorionic gonadotropin (hCG) |
| | IM-862 |
| | Interferon alpha/beta/gamma |
| | Interferon inducible protein (IP-10) |
| | Interleukin-12 |
| | Kringle 5 (plasminogen fragment) |
| | Marimastat |
| | Metalloproteinase inhibitors (TIMPs) |
| | 2-Methoxyestradiol |
| | MMI 270 (CGS 27023A) |
| | MoAb IMC-1C11 |
| | Neovastat |
| | NM-3 |
| | Panzem |
| | PI-88 |
| | Placental ribonuclease inhibitor |
| | Plasminogen activator inhibitor |
| | Platelet factor-4 (PF4) |
| | Prinomastat |
| | Prolactin 16kD fragment |
| | Proliferin-related protein (PRP) |
| | PTK 787/ZK 222594 |
| | Retinoids |
| | Solimastat |
| | Squalamine |
| | SS 3304 |
| | SU 5416 |
| | SU6668 |
| | SU11248 |
| | Tetrahydrocortisol-S |
| | Tetrathiomolybdate |
| | Thalidomide |

TABLE 2-continued

| | |
|---|---|
| | Thrombospondin-1 (TSP-1) |
| | TNP-470 |
| | Transforming growth factor-beta (TGF-β) |
| | Vasculostatin |
| | Vasostatin (calreticulin fragment) |
| | ZD6126 |
| | ZD 6474 |
| | farnesyl transferase inhibitors (FTI) |
| | Bisphosphonates |
| Antimitotic agents: | Allocolchicine |
| | Halichondrin B |
| | Colchicine |
| | colchicine derivative |
| | dolstatin 10 |
| | Maytansine |
| | Rhizoxin |
| | Thiocolchicine |
| | trityl cysteine |
| Others: | |
| Isoprenylation inhibitors: | |
| Dopaminergic neurotoxins: | 1-methyl-4-phenylpyridinium ion |
| Cell cycle inhibitors: | Staurosporine |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | Verapamil |
| $Ca^{2+}$ ATPase inhibitors: | Thapsigargin |

Other additional anticancer agents that can be used in the compositions and methods of the present invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine hydrochloride; hydroxyurea; idarubicin hydrochloride; ifosfamide; ilmofosine; interleukin-2 (including recombinant interleukin-2, or rIL2), interferon alfa-2α; interferon alfa-2β; interferon alfa-n1; interferon alfa-n3; interferon beta-Iα; interferon gamma-Iβ; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Further anticancer drugs that can be used in the methods and compositions of the invention include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta Lactam Derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-acytidine; dihydrotaxol; dioxamycin; diphenyl spiromustine; docetaxel; docosanol; dolasetron; doxifluridine; droloxifene; dronabinol; duocarmycin SA; ebselen; ecomustine;

edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agents; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In one another embodiment, the other anticancer agent is interferon-α.

In another embodiment, the other anticancer agent is interleukin-2.

In one embodiment, the other anticancer agent is an alkylating agent, such as a nitrogen mustard, a nitrosourea, an alkylsulfonate, a triazene, or a platinum-containing agent.

In one embodiment, the other anticancer agent is a triazene alkylating agent.

In a specific embodiment, the other anticancer agent is temozolomide.

Temozolomide can be administered to a subject at dosages ranging from about 60 mg/m$^2$ (of a subject's body surface area) to about 250 mg/m$^2$ and from about 100 mg/m$^2$ to about 200 mg/m$^2$. In specific embodiments, the dosages of temozolomide are about 10 mg/m$^2$, about 1 mg/m$^2$, about 5 mg/m$^2$, about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 210 mg/m$^2$, about 220 mg/m$^2$, about 230 mg/m$^2$, about 240 mg/m$^2$, or about 250 mg/m$^2$.

In a particular embodiment, temozolomide is administered orally.

In one embodiment, temozolomide is administered orally to a subject at a dose ranging from about 150 mg/m$^2$ to about 200 mg/m$^2$.

In another embodiment, temozolomide is administered orally to a subject once per day for five consecutive days at a dose ranging from about 150 mg/m$^2$ to about 200 mg/m$^2$.

In a specific embodiment, temozolomide is administered orally to a subject once per day for five consecutive days at a dose ranging from about 150 mg/m$^2$ to about 200 mg/m$^2$ on days 1-5, then again orally once per day for five consecutive days on days 28-32 at a dose ranging from about 150 mg/m$^2$ to about 200 mg/m$^2$, then again orally once per day for five consecutive days on days 55-59 at a dose ranging from about 150 mg/m² to about 200 mg/m².

In a specific embodiment, the other anticancer agent is procarbazine.

Procarbazine can be administered to a subject at dosages ranging from about 50 mg/m² (of a subject's body surface area) to about 100 mg/m² and from about 60 mg/m² to about 100 mg/m². In specific embodiments, the dosages of procarbazine are about 10 mg/m², about 1 mg/m², about 5 mg/m², about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 110 mg/m², about 120 mg/m², about 130 mg/m², about 140 mg/m², about 150 mg/m², about 160 mg/m², about 170 mg/m², about 180 mg/m², about 190 mg/m², about 200 mg/m², about 210 mg/m², about 220 mg/m², about 230 mg/m², about 240 mg/m², about 250 mg/m², about 260 mg/m², about 270 mg/m², about 280 mg/m², about 290 mg/m², about 300 mg/m², about 310 mg/m², about 320 mg/m², about 330 mg/m², about 340 mg/m², about 350 mg/m², about 360 mg/m², about 370 mg/m², about 380 mg/m², about 390 mg/m², about 400 mg/m², about 410 mg/m², about 420 mg/m², about 430 mg/m², about 440 mg/m², about 450 mg/m², about 460 mg/m², about 470 mg/m², about 480 mg/m², about 490 mg/m², or about 500 mg/m².

In a particular embodiment, procarbazine is administered intravenously.

In one embodiment, procarbazine is administered intravenously to a subject at a dose ranging from about 50 mg/m² to about 100 mg/m².

In another embodiment, procarbazine is administered intravenously to a subject once per day for five consecutive days at a dose ranging from about 50 mg/m² to about 100 mg/m².

In a specific embodiment, procarbazine is administered intravenously to a subject once per day for five consecutive days at a dose ranging from about 50 mg/m² to about 100 mg/m² on days 1-5, then again intravenously once per day for five consecutive days on days 28-32 at a dose ranging from about 50 mg/m² to about 100 mg/m², then again intravenously once per day for five consecutive days on days 55-59 at a dose ranging from about 50 mg/m² to about 100 mg/m².

In another embodiment, procarbazine is administered once intravenously to a subject at a dose ranging from about 50 mg/m² to about 100 mg/m².

In a specific embodiment, the other anticancer agent is dacarbazine.

Dacarbazine can be administered to a subject at dosages ranging from about 60 mg/m² (of a subject's body surface area) to about 250 mg/m² and from about 150 mg/m² to about 250 mg/m². In specific embodiments, the dosages of dacarbazine are about 10 mg/m², about 1 mg/m², about 5 mg/m², about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 110 mg/m², about 120 mg/m², about 130 mg/m², about 140 mg/m², about 150 mg/m², about 160 mg/m², about 170 mg/m², about 180 mg/m², about 190 mg/m², about 200 mg/m², about 210 mg/m², about 220 mg/m², about 230 mg/m², about 240 mg/m², about 250 mg/m², about 260 mg/m², about 270 mg/m², about 280 mg/m², about 290 mg/m², about 300 mg/m², about 310 mg/m², about 320 mg/m², about 330 mg/m², about 340 mg/m², about 350 mg/m², about 360 mg/m², about 370 mg/m², about 380 mg/m², about 390 mg/m², about 400 mg/m², about 410 mg/m², about 420 mg/m², about 430 mg/m², about 440 mg/m², about 450 mg/m², about 460 mg/m², about 470 mg/m², about 480 mg/m², about 490 mg/m², or about 500 mg/m².

In a particular embodiment, dacarbazine is administered intravenously.

In one embodiment, dacarbazine is administered intravenously to a subject at a dose ranging from about 150 mg/m² to about 250 mg/m².

In another embodiment, dacarbazine is administered intravenously to a subject once per day for five consecutive days at a dose ranging from about 150 mg/m² to about 250 mg/m².

In a specific embodiment, dacarbazine is administered intravenously to a subject once per day for five consecutive days at a dose ranging from about 150 mg/m² to about 250 mg/m² on days 1-5, then again intravenously once per day for five consecutive days on days 28-32 at a dose ranging from about 150 mg/m² to about 250 mg/m², then again intravenously once per day for five consecutive days on days 55-59 at a dose ranging from about 150 mg/m² to about 250 mg/m².

In one embodiment, dacarbazine is administered once intravenously to a subject at a dose ranging from about 150 mg/m² to about 250 mg/m².

In one embodiment, the other anticancer agent is a Topoisomerase I inhibitor, such as etoposide, teniposide, topotecan, irinotecan, 9-aminocamptothecin, camptothecin, or crisnatol.

In a specific embodiment, the other anticancer agent is irinotecan.

Irinotecan can be administered to a subject at dosages ranging from about 50 mg/m² (of a subject's body surface area) to about 150 mg/m² and from about 75 mg/m² to about 150 mg/m². In specific embodiments, the dosages of irinotecan are about 10 mg/m², about 1 mg/m², about 5 mg/m², about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 110 mg/m², about 120 mg/m², about 130 mg/m², about 140 mg/m², about 150 mg/m², about 160 mg/m², about 170 mg/m², about 180 mg/m², about 190 mg/m², about 200 mg/m², about 210 mg/m², about 220 mg/m², about 230 mg/m², about 240 mg/m², about 250 mg/m², about 260 mg/m², about 270 mg/m², about 280 mg/m², about 290 mg/m², about 300 mg/m², about 310 mg/m², about 320 mg/m², about 330 mg/m², about 340 mg/m², about 350 mg/m², about 360 mg/m², about 370 mg/m², about 380 mg/m², about 390 mg/m², about 400 mg/m², about 410 mg/m², about 420 mg/m², about 430 mg/m², about 440 mg/m², about 450 mg/m², about 460 mg/m², about 470 mg/m², about 480 mg/m², about 490 mg/m², or about 500 mg/m².

In a particular embodiment, irinotecan is administered intravenously.

In one embodiment, irinotecan is administered intravenously to a subject at a dose ranging from about 50 mg/m² to about 150 mg/m².

In another embodiment, irinotecan is administered intravenously to a subject once per day for five consecutive days at a dose ranging from about 50 mg/m² to about 150 mg/m².

In a specific embodiment, irinotecan is administered intravenously to a subject once per day for five consecutive days at a dose ranging from about 50 mg/m² to about 150 mg/m² on days 1-5, then again intravenously once per day for five consecutive days on days 28-32 at a dose ranging from about 50 mg/m² to about 150 mg/m², then again intravenously once per day for five consecutive days on days 55-59 at a dose ranging from about 50 mg/m² to about 150 mg/m².

In one embodiment, the invention provides administration of an effective amount of: (i) a Tetracyclic Amino Compound or a Tetracyclic Carboxamido Compound and (ii) one or more other anticancer agents.

In one embodiment, (i) a Tetracyclic Amino Compound or a Tetracyclic Carboxamido Compound and (ii) one or more other anticancer agents are administered in doses commonly employed when such agents are used as monotherapy for the treatment of cancer.

In another embodiment, (i) a Tetracyclic Amino Compound or a Tetracyclic Carboxamido Compound and (ii) one or more other anticancer agents act synergistically and are administered in doses that are less than the doses commonly employed when such agents are used as monotherapy for the treatment of cancer.

The dosage of the (i) Tetracyclic Amino Compound or the Tetracyclic Carboxamido Compound and (ii) one or more other anticancer agents administered as well as the dosing schedule can depend on various parameters, including, but not limited to, the cancer being treated, the patient's general health, and the administering physician's discretion.

In one embodiment, the other anticancer agent is O-6-benzylguanine.

In another embodiment, the other anticancer agent is O-6-benzylguanine and temozolomide.

In another embodiment, the other anticancer agent is O-6-benzylguanine and procarbazine.

In still another embodiment, the other anticancer agent is O-6-benzylguanine and dacarbazine.

4.5.10.3 Multi-Therapy for Cancer

The Tetracyclic Amino Compounds or the Tetracyclic Carboxamido Compounds can be administered to a subject that has undergone or is currently undergoing one or more additional anticancer therapies including, but not limited to, surgery, radiation therapy, or immunotherapy, such as cancer vaccines.

In one embodiment, the invention provides methods for treating or preventing cancer comprising administering to a subject in need thereof (a) an amount of a Tetracyclic Amino Compound or a Tetracyclic Carboxamido Compound effective to treat or prevent cancer; and (b) another anticancer therapy including, but not limited to, surgery, radiation therapy, or immunotherapy, such as a cancer vaccine.

In one embodiment, the other anticancer therapy is radiation therapy.

In another embodiment, the other anticancer therapy is surgery.

In still another embodiment, the other anticancer therapy is immunotherapy.

In a specific embodiment, the present methods for treating or preventing cancer comprise administering (i) an effective amount of a Tetracyclic Amino Compound or Tetracyclic Carboxamido Compound and (ii) radiation therapy. The radiation therapy can be administered concurrently with, prior to, or subsequent to the Tetracyclic Amino Compound or the Tetracyclic Carboxamido Compound, in one embodiment at least an hour, five hours, 12 hours, a day, a week, a month, in another embodiment several months (e.g., up to three months), prior or subsequent to administration of the Tetracyclic Amino Compound or the Tetracyclic Carboxamido Compounds.

Where the other anticancer therapy is radiation therapy, any radiation therapy protocol can be used depending upon the type of cancer to be treated. For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered.

Additionally, the invention provides methods of treatment of cancer using a Tetracyclic Amino Compound or a Tetracyclic Carboxamido Compound as an alternative to chemotherapy or radiation therapy where the chemotherapy or the radiation therapy results in negative side effects in the subject being treated. The subject being treated can, optionally, be treated with another anticancer therapy such as surgery, radiation therapy, or immunotherapy.

The Tetracyclic Amino Compounds or the Tetracyclic Carboxamido Compounds can also be used in vitro or ex vivo, such as for the treatment of certain cancers, including, but not limited to leukemias and lymphomas, such treatment involving autologous stem cell transplants. This can involve a process in which the subject's autologous hematopoietic stem cells are harvested and purged of all cancer cells, the subject's remaining bone-marrow cell population is then eradicated via the administration of a Tetracyclic Amino Compound or a Tetracyclic Carboxamido Compound and/or radiation, and the resultant stem cells are infused back into the subject. Supportive care can be subsequently provided while bone marrow function is restored and the subject recovers.

4.6 Therapeutic/Prophylactic Administration and Compositions of the Invention Due to their activity, The Tetracyclic Amino Compounds and the Tetracyclic Carboxamido Compounds are advantageously useful in veterinary and human medicine. As described above, The Tetracyclic Amino Compounds or the Tetracyclic Carboxamido Compounds are useful for treating or preventing a Condition in a subject in need thereof.

The Tetracyclic Amino Compounds or the Tetracyclic Carboxamido Compounds can be administered in amounts that are effective to treat or prevent a Condition in a subject.

When administered to a subject, The Tetracyclic Amino Compounds or the Tetracyclic Carboxamido Compounds can be administered as a component of a composition that comprises a physiologically acceptable carrier or vehicle. The present compositions, which comprise a Tetracyclic Amino Compound or a Tetracyclic Carboxamido Compound, can be administered orally. The Tetracyclic Amino Compounds or the Tetracyclic Carboxamido Compounds can also be administered by any other convenient route, for example, by infusion or bolus injection, by absorption through epithelial or mucocutaneous linings (e.g., oral, rectal, and intestinal mucosa) and can be administered together with another biologically active agent. Administration can be systemic or local. Various delivery systems are known, e.g., encapsulation in liposomes, microparticles, microcapsules, capsules, and can be administered.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result in the release of a Tetracyclic Amino Compound or a Tetracyclic Carboxamido Compound into the bloodstream.

In one embodiment, The Tetracyclic Amino Compounds or the Tetracyclic Carboxamido Compounds are administered orally.

In other embodiments, it can be desirable to administer the Tetracyclic Amino Compounds or the Tetracyclic Carboxamido Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Tetracyclic Amino Compounds or the Tetracyclic Carboxamido Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon oar, synthetic pulmonary surfactant. In certain embodiments, the Tetracyclic Amino Compounds or the Tetracyclic Carboxamido Compounds can be formulated as a suppository, with traditional binders and excipients such as triglycerides.

In another embodiment The Tetracyclic Amino Compounds or the Tetracyclic Carboxamido Compounds can be delivered in a vesicle, in particular a liposome (see Langer, *Science* 249:1527-1533 (1990) and Treat or prevent et al., *Liposomes in Therapy of Infectious Disease and Cancer* 317-327 and 353-365 (1989)).

In yet another embodiment the Tetracyclic Amino Compounds or the Tetracyclic Carboxamido Compounds can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-1533 (1990) can be used. In one embodiment a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190. (1935); During et al., *Ann. Neural.* 25:351 (1989); and Howard et al., *J. Neurosurg.* 71:105 (1989)).

In yet another embodiment a controlled- or sustained-release system can be placed in proximity of a target of the Tetracyclic Amino Compounds or the Tetracyclic Carboxamido Compounds, e.g., the spinal column, brain, skin, lung, or gastrointestinal tract, thus requiring only a fraction of the systemic dose.

The present compositions can optionally comprise a suitable amount of a pharmaceutically acceptable excipient so as to provide the form for proper administration to the subject.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia; gelatin, starch paste, talc, keratin, colloidal silica, urea and the like. In addition, auxiliary, stabilizing, thickening, lubricating, and coloring agents can be used. In one embodiment the pharmaceutically acceptable excipients are sterile when administered to a subject. Water is a particularly useful excipient when the Tetracyclic Amino Compound or the Tetracyclic Carboxamido Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills; pellets, capsules, capsules containing liquids, powders, sustained-release formulations, suppositories, emulsions. aerosols, sprays, suspensions, or any other form suitable for use. In one embodiment the composition is in the form of a capsule (see e.g. U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

In one embodiment the Tetracyclic Amino Compounds or the Tetracyclic Carboxamido Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving a Tetracyclic Amino Compound or a Tetracyclic Carboxamido Compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment the Tetracyclic Amino Compounds or the Tetracyclic Carboxamido Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized-powder or water free concentrate in a hermetically sealed container such as an ampule or sachette indicating the quantity of active agent. Where the Tetracyclic Amino Compounds or the Tetracyclic Carboxamido Compounds are to be administered by infusion, they can be dispensed, for example, with an infusion bottle containing sterile pharmaceutical grade water or saline. Where the Tetracyclic Amino Compounds or the Tetracyclic Carboxamido Compounds are administered by injection, an ampule of sterile water for injection or saline can be provided so that the ingredients can be mixed prior to administration.

The Tetracyclic Amino Compounds and the Tetracyclic Carboxamido Compounds can be administered by controlled-release or sustained-release means or by delivery devices that are well known to those of ordinary skill in the art. Examples include, but arc not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354;556; and 5,733,556, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of a Tetracyclic Amino Compound or a Tetracyclic Carboxamido Compound to treat or prevent the Condition in a minimal amount of time. Advantages of controlled- or sustained-release compositions include extended activity of the drug, reduced dosage frequency, and increased subject compliance. In addition, controlled- or sustained-release compositions can favorably affect the time of onset of action or other characteristics, such as blood levels of the Tetracyclic Amino Compound or the Tetracyclic Carboxamido Compound, and can thus reduce the occurrence of adverse side effects.

Controlled- or sustained-release compositions can initially release an amount of a Tetracyclic Amino Compound or a Tetracyclic Carboxamido Compound that promptly produces the desired therapeutic or prophylactic effect, and gradually and continually release other amounts of the Tetracyclic Amino Compound or the Tetracyclic Carboxamido Compound to maintain this level of therapeutic or prophylactic effect over an extended period of time. To maintain a constant level of the Tetracyclic Amino Compound or the Tetracyclic Carboxamido Compound in the body, the Tetracyclic Amino Compound or the Tetracyclic Carboxamido Compound can be released from the dosage form at a rate that will replace the amount of Tetracyclic Amino Compound or Tetracyclic Carboxamido Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Tetracyclic Amino Compound or the Tetracyclic Carboxamido Compound that is effective in the treatment or prevention of a Condition can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of the practitioner and each subject's circumstances in view of, e.g., published clinical studies. Suitable effective dosage amounts, however, range from about 10 micrograms to about 5 grams about every 4 h, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one Tetracyclic Amino Compound or Tetracyclic Carboxamido Compound is administered, the effective dosage amounts correspond to the total amount administered.

Compositions can be prepared according to conventional mixing, granulating or coating methods, respectively, and the present compositions can contain, in one embodiment, from about 0.1% to about 99%; and in another embodiment from about 1% to about 70% of the Tetracyclic Amino Compound or the Tetracyclic Carboxamido Compound by weight or volume.

The dosage regimen utilizing the Tetracyclic Amino Compound or the Tetracyclic Carboxamido Compound can be selected in accordance with a variety of factors including type, species, age, weight, sex and medical condition of the subject; the severity of the condition to be treated; the route of administration; the renal or hepatic function of the subject; and the particular Tetracyclic Amino Compound or Tetracyclic Carboxamido Compound employed. A person skilled in the art can readily determine the effective amount of the drug useful for treating or preventing the Condition.

The Tetracyclic Amino Compounds or the Tetracyclic Carboxamido Compounds can be administered in a single daily dose, or the total daily dosage can be administered in divided doses of two, three or four times daily. Furthermore, the Tetracyclic Amino Compounds or the Tetracyclic Carboxamido Compounds can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of Tetracyclic Amino Compound or Tetracyclic Carboxamido Compound ranges from about 0.1% to about 15%, w/w or w/v.

In one embodiment, the compositions comprise an amount of (i) a Tetracyclic Amino Compound or a Tetracyclic Carboxamido Compound and (ii) the other anticancer agent which together are effective to treat or prevent cancer. In another embodiment, the amount of (i) a Tetracyclic Amino Compound or a Tetracyclic Carboxamido Compound and (ii) the other anticancer agent is at least about 0.01% of the combined combination chemotherapy agents by weight of the composition. When intended for oral administration, this amount can be varied from about 0.1% to about 80% by weight of the composition. Some oral compositions can comprise from about 4% to about 50% of combined amount of (i) a Tetracyclic Amino Compound or a Tetracyclic Carboxamido Compound and (ii) the other anticancer agent by weight of the composition. Other compositions of the present invention are prepared so that a parenteral dosage unit contains from about 0.01% to about 2% by weight of the composition.

The Tetracyclic Amino Compounds or the Tetracyclic Carboxamido Compounds can be assayed in vitro or in vivo for the desired therapeutic or prophylactic activity prior to use in humans. Animal model systems can be used to demonstrate safety and efficacy.

The present methods for treating or preventing a Condition in a subject in need thereof can further comprise administering another prophylactic or therapeutic agent to the subject being administered a Tetracyclic Amino Compound or a Tetracyclic Carboxamido Compound. In one embodiment the other prophylactic or therapeutic agent is administered in an effective amount. The other prophylactic or therapeutic agent includes, but is not limited to, an anti-inflammatory agent, an anti-renal failure agent, an anti-diabetic agent, and anti-cardiovascular disease agent, an antiemetic agent, a hematopoietic colony stimulating factor, an anxiolytic agent, and an analgesic agent.

In one embodiment, the other prophylactic or therapeutic agent is an agent useful for reducing any potential side effect of a Tetracyclic Amino Compound or a Tetracyclic Carboxamido Compound. Such potential side effects include, but are not limited to, nausea, vomiting, headache, low white blood cell count, low red blood cell count, low platelet count, headache, fever, lethargy, muscle aches, general pain, bone pain, pain at an injection site, diarrhea, neuropathy, pruritis, mouth sores, alopecia, anxiety or depression.

In one embodiment, the Tetracyclic Amino Compound or Tetracyclic Carboxamido Compound can be administered prior to, concurrently with, or after an anti-inflammatory agent, or on the same day, or within 1 hour, 2 hours, 12 hours, 24 hours, 48 hours or 72 hours of each other.

In another embodiment, the Tetracyclic Amino Compound or Tetracyclic Carboxamido Compound can be administered prior to, concurrently with, or after an anti-renal failure agent, or on the same day, or within 1 hour, 2 hours, 12 hours, 24 hours, 48 hours or 72 hours of each other.

In still another embodiment, the Tetracyclic Amino Compound or Tetracyclic Carboxamido Compound can be administered prior to, concurrently with, or after an anti-diabetic agent, or on the same day, or within 1 hour, 2 hours, 12 hours, 24 hours, 48 hours or 72 hours of each other.

In yet another embodiment, the Tetracyclic Amino Compound or Tetracyclic Carboxamido Compound can be administered prior to, concurrently with, or after an anti-cardiovascular disease agent, or on the same day, or within 1 hour, 2 hours, 12 hours, 24 hours, 48 hours or 72 hours of each other.

In a further embodiment, the Tetracyclic Amino Compound or Tetracyclic Carboxamido Compound can be administered prior to, concurrently with, or after an antiemetic agent, or on the same day, or within 1 hour, 2 hours, 12 hours, 24 hours, 48 hours or 72 hours of each other.

In another embodiment, the Tetracyclic Amino Compound or Tetracyclic Carboxamido Compound can be administered prior to, concurrently with, or after a hematopoietic colony stimulating factor, or on the same day, or within 1 hour, 2 hours, 12 hours, 24 hours, 48 hours, 72 hours, 1 week, 2 weeks, 3 weeks or 4 weeks of each other.

In still embodiment, the Tetracyclic Amino Compound or Tetracyclic Carboxamido Compound can be administered prior to, concurrently with, or after an opioid or non-opioid analgesic agent, or on the same day, or within 1 hour, 2 hours, 12 hours, 24 hours, 48 hours or 72 hours of each other.

In yet another embodiment, the Tetracyclic Amino Compound or Tetracyclic Carboxamido Compound can be administered prior to, concurrently with, or after an anxiolytic agent, or on the same day, or within 1 hour, 2 hours, 12 hours, 24 hours, 48 hours or 72 hours of each other.

Effective amounts of the other prophylactic or therapeutic agents are well known to those skilled in the art. However, it is well within the skilled artisan's purview to determine the other prophylactic or therapeutic agent's optimal effective amount range. In one embodiment of the invention, where another prophylactic or therapeutic agent is administered to a subject, the effective amount of the Tetracyclic Amino Compound or the Tetracyclic Carboxamido Compound is less than its effective amount would be where the other prophylactic or therapeutic agent is not administered. In this case, without being bound by theory, it is believed that The Tetracyclic Amino Compounds or the Tetracyclic Carboxamido Compounds and the other prophylactic or therapeutic agent act synergistically to treat or prevent a Condition.

Anti-inflammatory agents useful in the methods of the present invention include but are not limited to adrenocorticosteroids, such as cortisol, cortisone, fludrocortisone, prednisone, prednisolone, 6α-methylprednisolone, triamcinolone, betamethasone, and dexamethasone; and non-steroidal anti-inflammatory agents (NSAIDs), such as aspirin, acetaminophen, indomethacin, sulindac, tolmetin, diclofenac, ketorolac, ibuprofen, naproxen, flurbiprofen, ketoprofen, fenoprofen, oxaprozin, mefenamic acid, meclofenamic acid, piroxicam, meloxicam, nabumetone, rofecoxib, celecoxib, etodolac, and nimesulide.

Anti-renal failure agents useful in the methods of the present invention include include but are not limited to ACE (angiotensin-converting enzyme) inhibitors, such as captopril, enalaprilat, lisinopril, benazepril, fosinopril, trandolapril, quinapril, and ramipril; diuretics, such as mannitol, glycerin, furosemide, toresemide, tripamide, chlorothiazide, methyclothiazide, indapamide, amiloride, and spironolactone; and fibric acid agents, such as clofibrate, gemfibrozil, fenofibrate, ciprofibrate, and bezafibrate.

Anti-diabetic agents useful in the methods of the present invention include include but are not limited to glucagons; somatostatin; diazoxide; sulfonylureas, such as tolbutamide, acetohexamide, tolazamide, chloropropamide, glybenclamide, glipizide, gliclazide, and glimepiride; insulin secretagogues, such as repaglinide, and nateglinide; biguanides, such as metformin and phenformin; thiazolidinediones, such as pioglitazone, rosiglitazone, and troglitazone; and α-glucosidase inhibitors, such as acarbose and miglitol.

Anti-cardiovascular disease agents useful in the methods of the present invention include include but are not limited to carnitine; thiamine; and muscarinic receptor antagonists, such as atropine, scopolamine, homatropine, tropicamide, pirenzipine, ipratropium, tiotropium, and tolterodine.

Antiemetic agents useful in the methods of the present invention include include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Hematopoietic colony stimulating factors useful in the methods of the present invention include, but are not limited to, filgrastim, sargramostim, molgramostim and epoietin alfa.

Opioid analgesic agents useful in the methods of the present invention include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene.

Non-opioid analgesic agents useful in the methods of the present invention include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

Anxiolytic agents useful in the methods of the present invention include, but are not limited to, buspirone, and benzodiazepines such as diazepam, lorazepam, oxazapam, chlorazepate, clonazepam, chlordiazepoxide and alprazolam.

4.7 Kits

The invention encompasses kits that can simplify the administration of a Tetracyclic Amino Compound or a Tetracyclic Carboxamido Compound to a subject.

A typical kit of the invention comprises a unit dosage form of a Tetracyclic Amino Compound or a Tetracyclic Carboxamido Compound. In one embodiment the unit dosage form is a container, which can be sterile, containing an effective amount of a Tetracyclic Amino Compound or a Tetracyclic Carboxamido Compound and a physiologically acceptable carrier or vehicle. The kit can further comprise a label or printed instructions instructing the use of the Tetracyclic Amino Compound or the Tetracyclic Carboxamido Compound to treat or prevent a Condition. The kit can also further comprise a unit dosage form of another prophylactic or therapeutic agent, for example, a container containing an effective amount of the other prophylactic or therapeutic agent. In one embodiment the kit comprises a container containing an effective amount of a Tetracyclic Amino Compound or a Tetracyclic Carboxamido Compound and an effective amount of another prophylactic or therapeutic agent. Examples of other prophylactic or therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The invention is further described in the following examples, which do not limit the scope of the invention described in the claims. The following examples can demonstrate the usefulness of the Tetracyclic Amino Compounds and Tetracyclic Carboxamido Compounds for treating or preventing a Condition.

5. EXAMPLES

Example 1 a) General Methods

Proton nuclear magnetic resonance ($^1$H NMR) spectra were obtained from Varian 300 MHz spectrophotometer and chemical shift is reported in parts per million, δ. Thin layer chromatography, TLC, was carried out on precoated TLC plates with silica gel 60 F-254 and preparative TLC on precoated Whatman 60A TLC plates. All intermediates and final compounds were characterized on the basis of $^1$H NMR.

b) Methyl 5,6-dihydro-5-oxo-11-H-indeno[1,2-c]isoquinoline-10-carboxylate (17a)

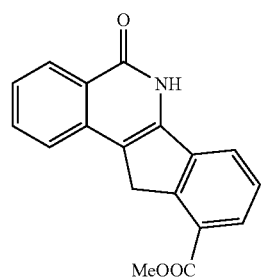

17a

A mixture of methyl 2-bromomethyl-3-cyanobenzoate (14.1 g, 55.5 mmol) and homophthalic anhydride (22.5 g, 138.8 mmol) in acetonitrile (150 ml) was stirred at room temperature, and a solution of triethylamine (23.2 ml) in acetonitrile (100 ml) was added dropwise to the mixture over the period of 1 h. After the completion of addition, the resultant suspension was refluxed for 4 hours. The reaction mixture was then cooled down to room temperature and filtered. The filtered solid was washed thoroughly with acetonitrile (100 ml) and ethanol (2×100 ml) and dried under vacuum at 50° C. Compound 17a was obtained in 81% yield (13.1 g). $^1$H NMR (DMSO-d$_6$): δ 12.21 (s, 1H); 8.20 (m, 2H); 7.83 (d, J=7.5 Hz, 1H); 7.71 (m, 2H); 7.47 (m, 2H); 4.07 (s, 2H); 3.89 (s, 3H).

c) Methyl 5,6-dihydro-5-oxo-11-H-indeno[1,2-c]isoquinoline-9-carboxylate (18a)

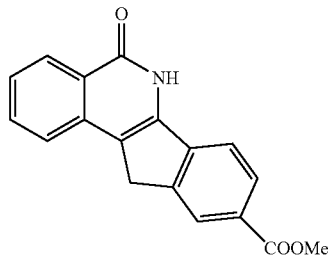

18a

Compound 18a was prepared from methyl 3-bromomethyl-4-cyanobenzoate in 65% yield. The reaction was carried out according to the procedure for preparing methyl 5,6-dihydro-5-oxo-11-H-indeno[1,2-c]isoquinoline-10-carboxylate (17a). $^1$H NMR (DMSO-$d_6$): δ 12.35 (s, 1H); 8.25 (d, J=8.1 Hz, 1H); 8.11 (s, 1H); 8.06 (d, J=7.8 Hz, 1H); 7.98 (d, J=8.1 Hz, 1H); 7.75 (m, 2H); 7.49 (m, 1H); 3.95 (s, 2H); 3.85 (s, 3H).

d) 5,6-dihydro-5-oxo-11-H-indeno[1,2-c]isoquinoline-10carboxylic acid (18b)

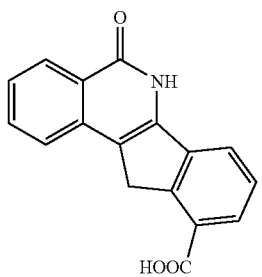

18b

A suspension of Compound 18a in a mixture of methanol and 1M NaOH solution was refluxed for 1 h. Additional water was added, and the resultant mixture was refluxed for another 1 h. The resultant clear solution was cooled to room temperature and 1M HCl solution was added under stirring. The resultant solid was filtered and washed with water and methanol and dried to provide Compound 18b. $^1$H NMR (DMSO-$d_6$): δ 12.38 (s, 1H); 8.25 (d, J=7.8 Hz, 1H); 8.11 (s, 1H); 8.04 (d, J=8.1 Hz, 1H); 7.97 (d, J=8.1 Hz, 1H); 7.76 (d, J=3.6 Hz, 2H); 7.51 (m, 1H); 3.97 (s, 2H).

e) 5,6-dihydro-5-oxo-11-H-indeno[1,2-c]isoquinoline-9-carboxylic acid

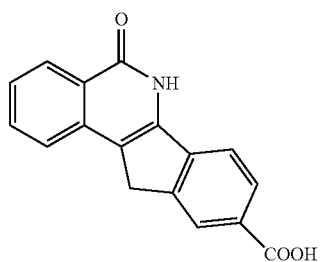

The above compound was made according to the procedure for preparing 5,6-dihydro-5-oxo-11-H-indeno[1,2-c]isoquinoline-10-carboxylic acid (18b), but using Compound 18a in place of Compound 17a. $^1$H NMR (DMSO-$d_6$): δ 12.34 (s, 1H); 8.24 (d, J=8.1 Hz, 1H); 8.20 (d, J=7.5 Hz 1H); 7.88 (d, J=7.8 Hz, 1H); 7.77 (m, 2H); 7.54 (d, J=7.8 Hz, 2H); 7.49 (d, J=8.1 Hz, 1H); 4.18 (s, 2H).

f) General Procedure for the Coupling of the Amine to the Carboxylic Acid

A suspension of $C_9$ or $C_{10}$—COOH and carbodiimide in dioxane was stirred at room temperature for 10 min. The relevant amine was added and the reaction mixture was stirred overnight at room temperature. The resultant solid was filtered, washed with dioxane and dried in a vacuum oven for 3 h. The following compounds are illustrative of the synthesis of Tetracyclic Carboxamido Compounds of Formulas (IIc) and (IId):

|  | $C_9$ Position | $C_{10}$ Position |
|---|---|---|
| 14a | CONH(CH$_2$)$_2$morpholine | H |
| 14b | CONH(CH$_2$)$_3$morpholine | H |
| 13b | CONH(CH$_2$)$_3$NMe$_2$ | H |
| 16a | H | CONH(CH$_2$)$_2$morpholine |
| 16b | H | CONH(CH$_2$)$_3$morpholine |
| 15a | H | CONH(CH$_2$)$_2$NMe$_2$ |
| 15b | H | CONH(CH$_2$)$_3$NMe$_2$ |

Compound 14a:
$^1$H NMR (DMSO-$d_6$): δ 8.25(d, J=8.1Hz, 1H); 8.09(s, 1H); 7.97(q, J=7.9Hz, 2H); 7.76(d, J=3.9Hz, 2H); 7.48(m, 1H); 3.94(s, 2H); 3.56(t, J=4.7Hz, 4H); 2.77(t, J=6.0Hz, 2H); 2.40-2.33(m, 6H).
Compound 14b:
$^1$H NMR (DMSO-$d_6$): δ 8.24(d, J=8.1Hz, 1H); 8.07(s, 1H); 7.92(m, 2H); 7.75(d, J=3.6Hz, 2H); 7.46(m, 1H); 3.91(s, 2H); 3.54(t, J=4.5Hz, 4H); 2.73(t, J=6.9Hz, 2H); 2.31(m, 6H); 1.62(t, J=6.9Hz, 2H).
Compound 13b:
$^1$H NMR (DMSO-$d_6$): δ 8.23(d, J=8.1Hz, 1H); 8.06(s, 1H); 7.90(m, 2H); 7.73(m, 2H); 7.45(m, 1H); 3.89(s, 2H); 2.71(t, J=6.9Hz, 4H); 2.23(t, J=6.6Hz, 2H); 2.09(s, 6H); 1.59(t, J=6.9Hz, 2H).
Compound 16a:
$^1$H NMR (DMSO-$d_6$): δ 8.23(d, J=8.1Hz, 1H); 8.03(d, J=7.5Hz, 1H); 7.80 (d, J=7.8Hz, 1H); 7.74(m, 2H); 7.47-7.36(m, 2H); 4.15(s, 2H); 3.54(m, 4H); 2.78(t, J=6.0Hz, 2H); 2.41-2.30(m, 6H).
Compound 16b:
$^1$H NMR (DMSO-$d_6$): δ 8.22(d, J=7.8Hz, 1H); 7.98(d, J=7.2Hz, 1H); 7.79 (d, J=7.2Hz, 1H); 7.71(m, 2H); 7.42(m, 1H); 7.34(t, J=7.8Hz, 1H); 4.14(s, 2H); 2.82(t, J=6.9Hz, 2H); 2.29(m, 6H); 1.70(t, J=6.6Hz, 2H).
Compound 15a:
$^1$H NMR (DMSO-$d_6$): δ 8.22(d, J=8.1Hz, 1H); 8.03(d, J=7.2Hz, 1H); 7.80 (d, J=7.8Hz, 1H); 7.73(m, 2H); 7.44(m, 1H); 7.37(t, J=8.1Hz, 1H); 4.14(s, 2H); 2.79(t, 2H); 2.36(t, J=6.0Hz, 2H); 2.14(s, 6H).
Compound 15b:
$^1$H NMR (DMSO-$d_6$): δ 8.24(d, J=7.8Hz, 1H); 8.01(d, J=7.2Hz, 1H); 7.80 (d, J=8.1Hz, 1H); 7.73(d, J=3.3Hz, 2H); 7.44(m, 1H); 7.37(t, J=7.5Hz, 1H); 4.15(s, 2H); 2.77(t, J=6.9Hz, 2H); 2.26(t, J=6.9Hz, 2H); 2.10(s, 6H); 1.63(t, J=6.9Hz, 2H).

Example 2 g) Effect of Illustrative Tetracyclic Amino Compounds and Tetracyclic Carboxamido Compounds on in vitro PARS Activity The ability of an illustrative Tetracyclic Amino Compound or Tetracyclic Carboxamido Compound to inhibit PARS and prevent peroxynitrite induced cytotoxicity can be demonstrated using methods described in Virag et al., *Br. J. Pharmacol.* 1999, 126(3):769-77; and *Immunology* 1998, 94(3):345-55.

h) Cell Protection Assay

Raw murine macrophages were treated with an illustrative Tetracyclic Amino Compound or Tetracyclic Carboxamido Compound for 15 minutes prior to the addition of peroxynitrite (750 µM) for a further 15 minutes. For the measurement of PARS activity, the media were removed and replaced with 0.5 ml HEPES (pH 7.5) containing 0.01% digitonin and $^3$H-NAD (0.5 µCi ml$^{-1}$, final concentration of NAD$^+$ in buffer is 20 nM/L) for 20 minutes. The cells were then scraped from the wells and placed in Eppendorf tubes containing 200 µl of 50% (w/v) ice-cold trichloroacetic acid (TCA). The tubes were then placed at 4° C. After 4 hr the tubes were centrifuged at 1800 g for 10 minutes and the supernatant removed. The pellets were washed twice with 500 µl ice-cold 5% TCA. The pellets were solubilized in 250 µl NaOH (0.1 M) containing 2% SDS overnight at 37° C. and the PARS activity was then determined by measuring the radioactivity incorporated using a Wallac scintillation counter. The solubilized protein (250 µl) was mixed with 5 ml of scintillant (ScintiSafe Plus, Fisher Scientific) before being counted for 10 minutes. The $EC_{50}$ value was calculated from a dose-response curve.

TABLE 1

Inhibitory effect of illustrative Isoquinoline Compounds on cell protection

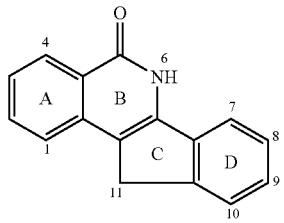

| | $C_9$ Position | $C_{10}$ Position | $EC_{50}$ µM |
|---|---|---|---|
| 14a | CONH(CH$_2$)$_2$morpholine | H | 1.1 |
| 14b | CONH(CH$_2$)$_3$morpholine | H | 1.1 |
| 13b | CONH(CH$_2$)$_3$NMe$_2$ | H | 0.9 |
| 16a | H | CONH(CH$_2$)$_2$morpholine | >1.5 |
| 16b | H | CONH(CH$_2$)$_3$morpholine | >1.5 |
| 15a | H | CONH(CH$_2$)$_2$NMe$_2$ | >1.5 |
| 15b | H | CONH(CH$_2$)$_3$NMe$_2$ | >1.5 |

Example 3 i) Effects of Tetracyclic Amino Compounds and Tetracyclic Carboxamido Compounds in an in vitro Model of Cell Death Using an in vitro, oxidant-stimulated thymocyte assay (described, in detail, in Virag et al., *Immunology* 94(3):345-55, 1998), an illustrative Tetracyclic Amino Compound or Tetracyclic Carboxamido Compound can be tested for its ability to prevent the oxidant-induced suppression of the viability of the cells and as such, this assay represents an in vitro model of reperfusion related cell death in ischemic organs.

Example 4 j) Effect of Tetracyclic Amino Compounds and Tetracyclic Carboxamido Compounds on in vivo Models of Inflammatory Diseases In order to substantiate the efficacy of the compounds in inflammatory diseases, the effect of an illustrative Tetracyclic Amino Compound or Tetracyclic Carboxamido Compound can be determined usng a systemic inflammatory model induced by bacterial lipopolysaccharide (LPS), which is reported to be responsible for causing reperfusion injurys and inflammatory diseases such as septic shock and systemic inflammatory response syndrome in animals (see Parrillo, *N. Engl. J. Med.*, 328:1471-1478 (1993) and Lamping, *J. Clin. Invest.* 101:2065-2071 (1998).

Example 5 k) Determination of the Effect of Tetracyclic Amino Compounds and Tetracyclic Carboxamido Compounds on in vivo Models of Reperfusion Injury The efficacy of an illustrative Tetracyclic Amino Compound or Tetracyclic Carboxamido Compound in a mouse model of ischemic and reperfused gut can be determined according to the method described in Liaudet et al., *Shock* 2000, 14(2):134-41.

In another set of experiments, the effect of an illustrative Tetracyclic Amino Compound or Tetracyclic Carboxamido Compound in a rat model of middle cerebral artery occlusion/reperfusion can be assayed as described in Abdelkarim et al., *Int J Mol Med.* 2001, 7(3):255-60.

Example 6 l) Effect of Illustrative Tetracyclic Amino Compounds and Tetracyclic Carboxamido Compounds in an in vivo Model of Diabetes PARS inhibitors and PARS deficiency are known to reduce the development of diabetes and the incidence of diabetic complications. In order to substantiate the efficacy of an illustrative Tetracyclic Amino Compound or Tetracyclic Carboxamido Compound in a diabetes model, a single high-dose streptozotocin model of diabetes can be used as conducted as described in Mabley et al., *Br J Pharmacol.* 2001, 133(6):909-9; and Soriano et al., *Nat Med.* 2001, 7(1):108-13. Briefly, 160 mg/kg streptozotocin is injected to mice treated with vehicle (control) or with an illustrative Tetracyclic Amino Compound or Tetracyclic Carboxamido Compound intraperitoneally (3 mg/kg) and 3 days later blood sugar levels are determined using a blood glucose meter.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparant to those skilled in the art and are intended to fall within the scope of the appended claims.

A number of references have been cited, the entire disclosures of which have been incorporated herein in their entirety.

What is claimed is:

1. A compound having the formula:

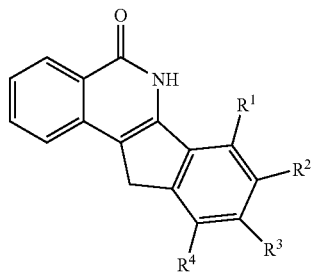

(I)

or a pharmaceutically acceptable salt thereof
wherein
one of the $R^1$, $R^2$, $R^3$ and $R^4$ groups is —NH(CH$_2$)$_n$—N(R$^5$)(R$^6$) and the remaining groups are simultaneously —H;

$R^5$ and $R^6$ are independently —H, —C$_1$-C$_6$ alkyl, or -phenyl, wherein the —C$_1$-C$_6$ alkyl, or -phenyl, is unsubstituted or substituted with one or more of -halo, —OH or —N(Z$_3$)(Z$_4$), where Z$_3$ and Z$_4$ are independently —H or —C$_1$-C$_5$ alkyl, which is unsubstituted or substituted with one or more of -halo, -hydroxy or —NH$_2$; or N, Z$_3$ and Z$_4$ are taken together to form an nitrogen-containing 3- to 7-membered monocyclic heterocycle which is unsubstituted or substituted with one to three of —C$_1$-C$_5$ alkyl, -halo, -halo-substituted C$_1$-C$_5$ alkyl, hydroxy, —O—C$_1$-C$_5$ alkyl, —N(R$^a$)$_2$, —COOH, —C(O)O—(C$_1$-C$_5$ alkyl), —OC(O)—(C$_1$-C$_5$ alkyl), —C(O)NH$_2$, or —NO$_2$, wherein each occurrence of R$^a$ is independently —H, -benzyl, or —C$_1$-C$_{10}$ alkyl; or N, R$^5$ and R$^6$ are taken together to form a nitrogen-containing 3- to 7-membered monocyclic heterocycle which is unsubstituted or substituted with one to three of —C$_1$-C$_5$ alkyl, -halo, halo-substituted C$_1$-C$_5$ alkyl, hydroxy, —O—C$_1$-C$_5$ alkyl, —N(R$^a$)$_2$,—COOH, —C(O)O—(C$_1$-C$_5$ alkyl), —OC(O)—(C$_1$-C$_5$ alkyl), —C(O)NH$_2$, or —NO$_2$, wherein each occurrence of R$^a$ is independently —H, benzyl, or —C$_1$-C$_{10}$ alkyl; and n is an integer ranging from 2 to 6.

2. The compound of claim 1, wherein $R^1$ is —NH(CH$_2$)$_n$—N(R$^5$)(R$^6$).

3. The compound of claim 1, wherein $R^2$ is —NH(CH$_2$)$_n$—N(R$^5$)(R$^6$).

4. The compound of claim 1, wherein $R^3$ is —NH(CH$_2$)$_n$—N(R$^5$)(R$^6$).

5. The compound of claim 1, wherein $R^4$ is —NH(CH$_2$)$_n$—N(R$^5$)(R$^6$).

6. The compound of claim 1, wherein $R^5$ is and $R^6$ are each C$_1$-C$_6$ alkyl.

7. The compound of claim 6, wherein $R^5$ and $R^6$ are each methyl.

8. The compound of claim 1, wherein n is 2.

9. The compound of claim 1, wherein n is 3.

10. The compound of claim 1, wherein $R^5$, $R^6$ and the nitrogen atom to which they are attached combine to form a morpholino group.

11. A compound having the formula:

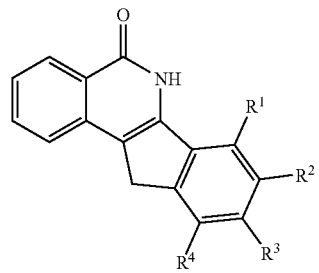

(II)

or a pharmaceutically acceptable salt thereof
wherein
one of the $R^1$, $R^2$, $R^3$ and $R^4$ groups is —C(O)NH(CH$_2$)$_n$—N(R$^5$)(R$^6$) and the remaining groups are simultaneously —H;

$R^5$ and $R^6$ are independently —H, —C$_1$-C$_6$ alkyl, -phenyl, or benzyl, wherein the —C$_1$-C$_6$ alkyl, -phenyl, is unsubstituted or substituted with one or more of -halo, —OH or —N(Z$_3$)(Z$_4$), where Z$_3$ and Z$_4$ are independently —H or —C$_1$-C$_5$ alkyl, which is unsubstituted or substituted with one or more of -halo, -hydroxy or —NH$_2$; or N, Z$_3$ and Z$_4$ are taken together to form an nitrogen-containing 3- to 7-membered monocyclic heterocycle which is unsubstituted or substituted with one to three of —C$_1$-C$_5$ alkyl, -halo, -halo-substituted C$_1$-C$_5$ alkyl, hydroxy, —O—C$_1$-C$_5$ alkyl, —N(R$^a$)$_2$, —COOH, —C(O)O—(C$_1$-C$_5$ alkyl), —OC(O)—(C$_1$-C$_5$ alkyl), —C(O)NH$_2$, or —NO$_2$, wherein each occurrence of R$^a$ is independently —H, -benzyl, or —C$_1$-C$_{10}$ alkyl; or N, R$^5$ and R$^6$ are taken together to form a nitrogen-containing 3- to 7-membered monocyclic heterocycle which is unsubstituted or substituted with one to three of —C$_1$-C$_5$ alkyl, halo, halo-substituted C$_1$-C$_5$ alkyl, hydroxy, —O—C$_1$-C$_5$ alkyl, —N(R$^a$)$_2$, —COOH, —C(O)O—(C$_1$-C$_5$ alkyl), —OC(O)—(C$_1$-C$_5$ alkyl), —C(O)NH$_2$, or —NO$_2$, wherein each occurrence of R$^a$ is independently —H, -benzyl, or —C$_1$-C$_{10}$ alkyl; and n is an integer ranging from 2 to 6.

12. The compound of claim 11, wherein $R^1$ is —C(O)NH(CH$_2$)$_n$—N(R$^5$)(R$^6$).

13. The compound of claim 11, wherein $R^2$ is —C(O)NH(CH$_2$)$_n$—N(R$^5$)(R$^6$).

14. The compound of claim 11, wherein $R^3$ is —C(O)NH(CH$_2$)$_n$—N(R$^5$)(R$^6$).

15. The compound of claim 11, wherein $R^4$ is —C(O)NH(CH$_2$)$_n$—N(R$^5$)(R$^6$).

16. The compound of claim 11, wherein $R^5$ is and $R^6$ are each C$_1$-C$_6$ alkyl.

17. The compound of claim 16 wherein $R^5$ is and $R^6$ are each methyl.

18. The compound of claim 11, wherein n is 2.

19. The compound of claim 11, wherein n is 3.

20. The compound of claim 11, wherein $R^5$, $R^6$ and the nitrogen atom to which they are attached, combine to form a morpholino group.

21. The compound of claim 1 having the structure:

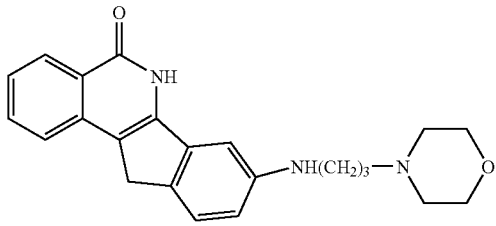

or a pharmaceutically acceptable salt thereof.

22. The compound of claim 11 having the structure:

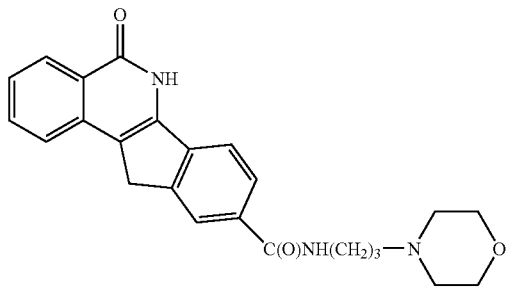

or a pharmaceutically acceptable salt thereof.

23. A composition comprising a physiologically acceptable carrier or vehicle and an effective amount of a compound or a pharmaceutically acceptable salt of a compound of claim 1.

24. A composition comprising a physiologically acceptable carrier or vehicle and an effective amount of a compound or a pharmaceutically acceptable salt of a compound of claim 11.

25. A composition comprising an effective amount of temozolomide, a physiologically acceptable carrier or vehicle, and an effective amount of a compound or a pharmaceutically acceptable salt of a compound having the formula:

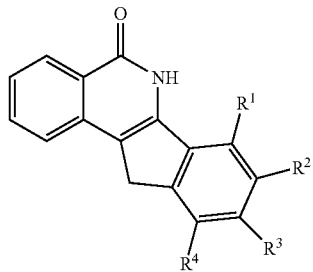

(II)

or a pharmaceutically acceptable salt thereof
wherein
one of the $R^1$, $R^2$, $R^3$ and $R^4$ groups is —C(O)NH$(CH_2)_n$—N($R^5$)($R^6$) and the remaining groups are simultaneously —H;
$R^5$ and $R^6$ are independently —H, —$C_1$-$C_6$ alkyl, -phenyl, or benzyl, wherein the —$C_1$-$C_6$ alkyl, -phenyl, or benzyl, is unsubstituted or substituted with one or more of -halo, —OH or —N($Z_3$)($Z_4$), where $Z_3$ and $Z_4$ are independently —H or —$C_1$-$C_5$ alkyl, which is unsubstituted or substituted with one or more of -halo, -hydroxy or —NH$_2$; or N, $Z_3$ and $Z_4$ are taken together to form an nitrogen-containing 3- to 7-membered monocyclic heterocycle which is unsubstituted or substituted with one to three of —$C_1$-$C_5$ alkyl, -halo, -halo-substituted $C_1$-$C_5$ alkyl, hydroxy, —O—$C_1$-$C_5$ alkyl, —N($R^a$)$_2$, —COOH, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; or N, $R^5$ and $R^6$ are taken together to form a nitrogen-containing 3- to 7-membered monocyclic heterocycle which is unsubstituted or substituted with one to three of —$C_1$-$C_5$ alkyl, phenyl, benzyl, hydroxy-substituted $C_1$-$C_5$ alkyl, -halo, -halo-substituted $C_1$-$C_5$ alkyl, halo-substituted phenyl, hydroxy, —O—$C_1$-$C_5$ alkyl, —(O—$C_1$-$C_5$-alkyl)-substituted phenyl, cyano-substituted phenyl, —N($R^a$)$_2$, —($C_1$-$C_5$ alkylene)-N($R^a$)$_2$, —COOH, —($C_1$-$C_5$ alkylene)-COOH, —($C_1$-$C_5$ alkylene)-C(O)O—$C_1$-$C_5$ alkyl, —($C_1$-$C_5$-alkylene)--C(O)NH—$C_1$-$C_5$ alkyl, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; and
n is an integer ranging from 2 to 6.

26. A composition comprising an effective amount of procarbazine, a physiologically acceptable carrier or vehicle, and an effective amount of a compound or a pharmaceutically acceptable salt of a compound having the formula:

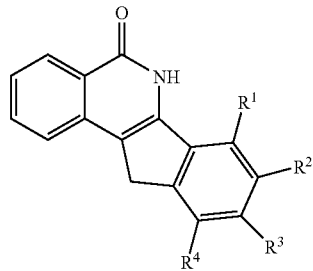

(II)

or a pharmaceutically acceptable salt thereof
wherein
one of the $R^1$, $R^2$, $R^3$ and $R^4$ groups is —C(O)NH$(CH_2)_n$—N($R^5$)($R^6$) and the remaining groups are simultaneously —H;
$R^5$ and $R^6$ are independently —H, —$C_1$-$C_6$ alkyl, -phenyl, or benzyl, wherein the —$C_1$-$C_6$ alkyl, -phenyl, or benzyl, is unsubstituted or substituted with one or more of -halo, —OH or —N($Z_3$)($Z_4$), where $Z_3$ and $Z_4$ are independently —H or —$C_1$-$C_5$ alkyl, which is unsubstituted or substituted with one or more of -halo, -hydroxy or —NH$_2$; or N, $Z_3$ and $Z_4$ are taken together to form an nitrogen-containing 3- to 7-membered monocyclic heterocycle which is unsubstituted or substituted with one to three of —$C_1$-$C_5$ alkyl, -halo, -halo-substituted $C_1$-$C_5$ alkyl, hydroxy, —O—$C_1$-$C_5$ alkyl, —N($R^a$)$_2$, —COOH, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; or N, $R^5$ and $R^6$ are taken together to form a nitrogen-containing 3- to 7-membered monocyclic heterocycle which is unsubstituted or substituted with one to three of —$C_1$-$C_5$ alkyl, phenyl, benzyl, hydroxy-substituted $C_1$-$C_5$ alkyl, -halo, -halo-substituted $C_1$-$C_5$ alkyl, halo-substituted phenyl, hydroxy, —O—$C_1$-$C_5$ alkyl, —(O—$C_1$-$C_5$-alkyl)-substituted phenyl, cyano-substituted phenyl, —N($R^a$)$_2$, —($C_1$-$C_5$ alkylene)-N($R^a$)$_2$, —COOH, —($C_1$-$C_5$ alkylene)-COOH, —($C_1$-$C_5$ alkylene)-C(O)O—$C_1$-$C_5$ alkyl, —($C_1$-$C_5$-alkylene)-C(O)NH—$C_1$-$C_5$ alkyl, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; and n is an integer ranging from 2 to 6.

27. A composition comprising an effective amount of dacarbazine, a physiologically acceptable carrier or vehicle, and an effective amount of a compound or a pharmaceutically acceptable salt of a compound having the formula:

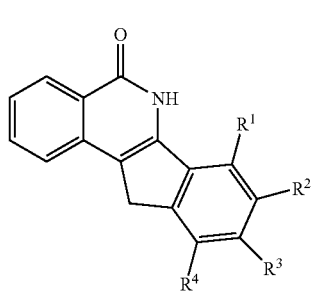

(II)

or a pharmaceutically acceptable salt thereof
wherein
one of the $R^1$, $R^2$, $R^3$ and $R^4$ groups is —C(O)NH(CH$_2$)$_n$—N($R^5$)($R^6$) and the remaining groups are simultaneously —H;
$R^5$ and $R^6$ are independently —H, —$C_1$-$C_6$ alkyl, -phenyl, or benzyl, wherein the —$C_1$-$C_6$ alkyl, -phenyl, or benzyl, is unsubstituted or substituted with one or more of -halo, —OH or —N($Z_3$)($Z_4$), where $Z_3$ and $Z_4$ are independently —H or —$C_1$-$C_5$ alkyl, which is unsubstituted or substituted with one or more of -halo, -hydroxy or —NH$_2$; or N, $Z_3$ and $Z_4$ are taken together to form an nitrogen-containing 3- to 7-membered monocyclic heterocycle which is unsubstituted or substituted with one to three of —$C_1$-$C_5$ alkyl, -halo, -halo-substituted $C_1$-$C_5$ alkyl, hydroxy, —O—$C_1$-$C_5$ alkyl, —N($R^a$)$_2$, —COOH, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; or —NO$_2$, wherein each occurrence of $R^a$ is independently —H, -benzyl, or —$C_1$-$C_{10}$ alkyl; or N, $R^5$ and $R^6$ are taken together to form a nitrogen-containing 3- to 7-membered monocyclic heterocycle which is unsubstituted or substituted with one to three of —$C_1$-$C_5$ alkyl, phenyl, benzyl, hydroxy-substituted $C_1$-$C_5$ alkyl, -halo, -halo-substituted $C_1$-$C_5$ alkyl, halo-substituted phenyl, hydroxy, —O—$C_1$-$C_5$ alkyl, —(O—$C_1$-$C_5$-alkyl)-substituted phenyl, cyano-substituted phenyl, —N($R^a$)$_2$, —($C_1$-$C_5$ alkylene)-N($R^a$)$_2$, —COOH, —($C_1$-$C_5$ alkylene)-COOH, —($C_1$-$C_5$ alkylene)-C(O)O—$C_1$-$C_5$ alkyl, —($C_1$-$C_5$-alkylene)-C(O)NH—$C_1$-$C_5$ alkyl, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; and
n is an integer ranging from 2 to 6.

28. A composition comprising an effective amount of irinotecan, a physiologically acceptable carrier or vehicle, and an effective amount of a compound or a pharmaceutically acceptable salt of a compound having the formula:

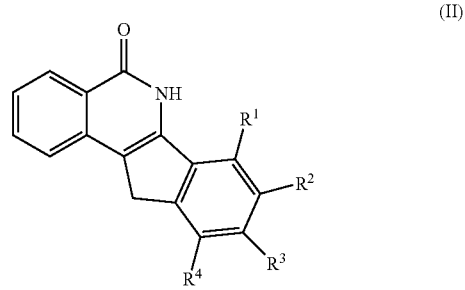

(II)

or a pharmaceutically acceptable salt thereof
wherein
one of the $R^1$, $R^2$, $R^3$ and $R^4$ groups is —C(O)NH(CH$_2$)$_n$—N($R^5$)($R^6$) and the remaining groups are simultaneously —H;
$R^5$ and $R^6$ are independently —H, —$C_1$-$C_6$ alkyl, -phenyl, or benzyl, wherein the —$C_1$-$C_6$ alkyl, -phenyl, or benzyl, is unsubstituted or substituted with one or more of -halo, —OH or —N($Z_3$)($Z_4$), where $Z_3$ and $Z_4$ are independently —H or —$C_1$-$C_5$ alkyl, which is unsubstituted or substituted with one or more of -halo, -hydroxy or —NH$_2$; or N, $Z_3$ and $Z_4$ are taken together to form an nitrogen-containing 3- to 7-membered monocyclic heterocycle which is unsubstituted or substituted with one to three of —$C_1$-$C_5$ alkyl, -halo, -halo-substituted $C_1$-$C_5$ alkyl, hydroxy, —O—$C_1$-$C_5$ alkyl, —N($R^a$)$_2$, —COOH, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; or N, $R^5$ and $R^6$ are taken together to form a nitrogen-containing 3- to 7-membered monocyclic heterocycle which is unsubstituted or substituted with one to three of —$C_1$-$C_5$ alkyl, phenyl, benzyl, hydroxy-substituted $C_1$-$C_5$ alkyl, -halo, -halo-substituted $C_1$-$C_5$ alkyl, halo-substituted phenyl, hydroxy, —O—$C_1$-$C_5$ alkyl, —(O—$C_1$-$C_5$-alkyl)-substituted phenyl, cyano-substituted phenyl, —N($R^a$)$_2$, —($C_1$-$C_5$ alkylene)-N($R^a$)$_2$, —COOH, —($C_1$-$C_5$ alkylene)-COOH, —($C_1$-$C_5$ alkylene)-C(O)O—$C_1$-$C_5$ alkyl, —($C_1$-$C_5$-alkylene)-C(O)NH—$C_1$-$C_5$ alkyl, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; and
n is an integer ranging from 2 to 6.

29. A composition comprising an effective amount of interleukin-2, a physiologically acceptable carrier or vehicle, and an effective amount of a compound or a pharmaceutically acceptable salt of a compound having the formula:

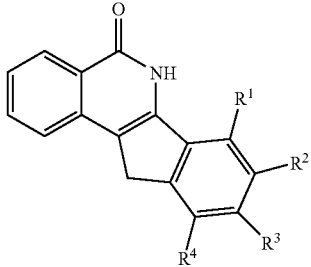

(II)

or a pharmaceutically acceptable salt thereof
wherein
one of the $R^1$, $R^2$, $R^3$ and $R^4$ groups is —C(O)NH$(CH_2)_n$—N($R^5$)($R^6$) and the remaining groups are simultaneously —H;

$R^5$ and $R^6$ are independently —H, —$C_1$-$C_6$ alkyl, -phenyl, or benzyl, wherein the —$C_1$-$C_6$ alkyl, -phenyl, or benzyl, is unsubstituted or substituted with one or more of -halo, —OH or —N($Z_3$)($Z_4$), where $Z_3$ and $Z_4$ are independently —H or —$C_1$-$C_5$ alkyl, which is unsubstituted or substituted with one or more of -halo, -hydroxy or —NH$_2$; or N, $Z_3$ and $Z_4$ are taken together to form an nitrogen-containing 3- to 7-membered monocyclic heterocycle which is unsubstituted or substituted with one to three of —$C_1$-$C_5$ alkyl, -halo, -halo-substituted $C_1$-$C_5$ alkyl, hydroxy, —O—$C_1$-$C_5$ alkyl, —N($R^a$)$_2$, —COOH, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; or N, $R^5$ and $R^6$ are taken together to form a nitrogen-containing 3- to 7-membered monocyclic heterocycle which is unsubstituted or substituted with one to three of —$C_1$-$C_5$ alkyl, phenyl, benzyl, hydroxy-substituted $C_1$-$C_5$ alkyl, -halo, -halo-substituted $C_1$-$C_5$ alkyl, halo-substituted phenyl, hydroxy, —O—$C_1$-$C_5$ alkyl, —(O—$C_1$-$C_5$-alkyl)-substituted phenyl, cyano-substituted phenyl, —N($R^a$)$_2$, —($C_1$-$C_5$ alkylene)-N($R^a$)$_2$, —COOH, —($C_1$-$C_5$ alkylene)-COOH, —($C_1$-$C_5$ alkylene)-C(O)O—$C_1$-$C_5$ alkyl, —($C_1$-$C_5$-alkylene)-C(O)NH—$C_1$-$C_5$ alkyl, —C(O)O—($C_1$-$C_5$ alkyl), —OC(O)—($C_1$-$C_5$ alkyl), —C(O)NH$_2$, or —NO$_2$, wherein each occurrence of $R^a$ is independently —H, -benzyl, or —$C_1$-$C_{10}$ alkyl; and
n is an integer ranging from 2 to 6.

* * * * *